United States Patent
Isler et al.

(10) Patent No.: US 9,464,902 B2
(45) Date of Patent: Oct. 11, 2016

(54) SYMBIOTIC UNMANNED AERIAL VEHICLE AND UNMANNED SURFACE VEHICLE SYSTEM

(71) Applicant: Regents of the University of Minnesota, Minneapolis, MN (US)

(72) Inventors: Volkan Isler, Minneapolis, MN (US); David Mulla, Minneapolis, MN (US); Pratap Tokekar, Minneapolis, MN (US); Joshua Vander Hook, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 319 days.

(21) Appl. No.: 14/498,369

(22) Filed: Sep. 26, 2014

(65) Prior Publication Data

US 2016/0018224 A1 Jan. 21, 2016

Related U.S. Application Data

(60) Provisional application No. 61/883,602, filed on Sep. 27, 2013.

(51) Int. Cl.
  *G01C 21/00* (2006.01)
  *G08G 7/00* (2006.01)
  *G01N 33/24* (2006.01)
  *G01N 1/02* (2006.01)

(52) U.S. Cl.
  CPC ............. *G01C 21/005* (2013.01); *G01C 21/00* (2013.01); *G01N 33/24* (2013.01); *G08G 7/00* (2013.01); *G01N 2001/021* (2013.01); *G01N 2033/245* (2013.01)

(58) Field of Classification Search
  CPC  G01C 21/005; H04B 1/7172; B64C 39/024; B64C 37/00; G01D 18/00; G01S 7/021; G06T 7/0002; G06Q 10/067
  USPC ............ 701/25; 342/353; 244/2, 116; 703/2; 455/130; 348/207.1; 705/4
  See application file for complete search history.

(56) References Cited

U.S. PATENT DOCUMENTS

| | | | |
|---|---|---|---|
| 2003/0164794 A1* | 9/2003 | Haynes | H04B 1/7172 342/353 |
| 2010/0193626 A1* | 8/2010 | Goossen | B64C 37/00 244/2 |
| 2011/0068224 A1* | 3/2011 | Kang | B64C 39/024 244/116 |
| 2012/0101784 A1* | 4/2012 | Lindores | G01D 18/00 703/2 |

(Continued)

OTHER PUBLICATIONS

."Clearpath robotics," 2013 (accessed Jan. 2013). [Online]. Available: http://clearpathrobotics.com.

(Continued)

*Primary Examiner* — Yuri Kan
(74) *Attorney, Agent, or Firm* — Theodore M. Magee; Westman, Champlin & Koehler, P.A.

(57) ABSTRACT

A system includes an unmanned aerial vehicle and an unmanned surface vehicle. The unmanned aerial vehicle has a memory storing a plurality of collection points and at least one sensor for collecting sensor data from each of the collection points. The unmanned surface vehicle is capable of moving to a plurality of locations. The unmanned aerial vehicle travels through the air between at least two collection points stored in the memory and the unmanned aerial vehicle is carried between at least two collection points stored in the memory by the unmanned surface vehicle.

17 Claims, 11 Drawing Sheets

(56) References Cited

U.S. PATENT DOCUMENTS

| | | | | |
|---|---|---|---|---|
| 2013/0157599 | A1* | 6/2013 | Ray | G01S 7/021 |
| | | | | 455/130 |
| 2015/0019267 | A1* | 1/2015 | Prieto | G06Q 10/067 |
| | | | | 705/4 |
| 2015/0379702 | A1* | 12/2015 | Ulman | G06T 7/0002 |
| | | | | 348/207.1 |

OTHER PUBLICATIONS

"Mikrokopter," 2013 (accessed Jan. 2013). [Online]. Available: http://mikrokopter.de.

"Spectrum Technologies Inc." 2013 (accessed Mar. 2013). [Online]. Available: http://www.specmeters.com/.

"Tetracam," 2014 (accessed Feb. 2014). [Online]. Available: www.tetracam.com.

Adamchuk, V.I., et al., "On-the-go soil sensors for precision agriculture," Computers and Electronics in Agriculture, vol. 44, No. 1, pp. 71-91, 2004.

Alt, H. et al., "Minimum-cost coverage of point sets by disks," in Proceedings of the Twenty-Second Annual Symposium on Computational geometry. ACM, 2006, pp. 449-458.

Applegate, D., et al., "Concorde TSP solver," URL http://www.tsp.gatech.edu/concorde, 2006.

Arkin, E.M., et al., "Approximation algorithms for the geometric covering salesman problem," Discrete Applied Mathematics, vol. 55, No. 3, pp. 197-218, 1994.

Arora, S., "Polynomial time approximation schemes for euclidean TSP and other geometric problems," in Foundations of Computer Science, 1996. Proceedings., 37th Annual Symposium on. IEEE, 1996, pp. 2-11.

Bhadauria, D., et al., "Robotic data mules for collecting data over sparse sensor fields," Journal of Field Robotics, vol. 28, No. 3, pp. 388-404, 2011.

Blum, A., et al., "Approximation algorithms for orienteering and discounted-reward TSP," SIAM Journal on Computing, vol. 37, No. 2, pp. 653-670, 2007.

Dumitrescu, A. et al., "Approximation algorithms for TSP with neighborhoods in the plane," Journal of Algorithms, vol. 48, No. 1, pp. 135-159, 2003.

Grocholsky, B., et al., "Cooperative air and ground surveillance," Robotics & Automation Magazine, IEEE, vol. 13, No. 3, pp. 16-25, 2006.

Krause, A., "SFO: A toolbox for submodular function optimization," The Journal of Machine Learning Research, vol. 11, pp. 1141-1144, 2010.

Krause, A., et al., "Near-optimal sensor placements in Gaussian processes: Theory, efficient algorithms and empirical studies," The Journal of Machine Learning Research, vol. 9, pp. 235-284, 2008.

Low, K.H., et al., "Decentralized active robotic exploration and mapping for probabilistic field classification in environmental sensing," in Proceedings of the 11th International Conference on Autonomous Agents and Multiagent Systems-vol. 1, 2012, pp. 105-112.

Meliou, A., et al., "Nonmyopic informative path planning in spatio-temporal models," in Proceedings of the 22nd national conference on Artificial intelligence-vol. 1. Association for the Advancement of Artificial Intelligence Press, 2007, pp. 602-607.

Mitchell, J.S., "Guillotine subdivisions approximate polygonal subdivisions: A simple polynomial-time approximation scheme for geometric tsp, k-MST, and related problems," SIAM Journal on Computing, vol. 28, No. 4, pp. 1298-1309, 1999.

Moran, M.S., et al., "Opportunities and limitations for image-based remote sensing in precision crop management,".Remote Sensing of Environment, vol. 61, No. 3, pp. 319-346, 1997.

Mulla, D., "Mapping and managing spatial patterns in soil fertility and crop yield," in Soil Specific Crop Management. American Society of Agronomy, 1993, pp. 15-26.

Mulla, D., et al., "Evaluation of remote sensing and targeted soil sampling for variable rate application of Lime," in Proceedings of 5th International Conference on Precision Agriculture. American Society of Agronomy, Crop Science Society of America, and Soil Science Society of America, 2001, 19 pages.

Mulla, D.J., "Twenty five years of remote sensing in precision agriculture: Key advances and remaining knowledge gaps," Biosystems Engineering, vol. 114, No. 4, pp. 358-371, 2013, special Issue: Sensing Technologies for Sustainable Agriculture.

Mustafa, N.H., et al., "Improved results on geometric hitting set problems," Discrete & Computational Geometry, vol. 44, No. 4, pp. 883-895, 2010.

Myers, D.E., "Estimation of linear combinations and co-kriging," Mathematical Geology, vol. 15, No. 5, pp. 633-637, 1983.

Randall, G.W., et al., "Nitrate nitrogen in surface waters as influenced by climatic conditions and agricultural practices," Journal of Environmental Quality, vol. 30, No. 2, pp. 337-344, 2001.

Rasmussen, C.E. et al., "Gaussian processes for machine learning (GPML) toolbox," The Journal of Machine Learning Research, vol. 11, pp. 3011-3015, 2010.

Rasmussen, C.E. et al., Chapter 4, Covariance Functions, MIT Press, pp. 79-104, 2006.

Rasmussen, C.E., Documentation for GPML Matlab Bode Version 3.5, http://gaussianprocess.org.gpml/code/matlab/doc/index.html, 12 pages, 2014.

Rasmussen, C.E. et al., "Chapter 2, Regression", MIT Press, pp. 8-32, 2006.

Singh, A., et al., "Nonmyopic Adaptive Informative Path Planning for Multiple Robots," International Joint Conference on Artificial Intelligence, pp. 1843-1850, 2008.

Song, D., et al., "Simultaneous localization of multiple unknown and transient radio sources using a mobile robot," Robotics, IEEE Transactions on, vol. 28, No. 3, pp. 668-680, 2012.

Sujit, P., et al., "An empirical evaluation of co-ordination strategies for an AUV and UAV," Journal of Intelligent & Robotic Systems, vol. 70, pp. 373-384, 2013.

Tanner, H.G., "Switched UAV-UGV cooperation scheme for target detection," IEEE International Conference on Robotics and Automation. 2007, pp. 3457-3462.

Tekdas, O., et al. "Efficient data collection from wireless nodes under the two-ring communication model," the International Journal of Robotics Research, vol. 31, No. 6, pp. 774-784, 2012.

Zhang, B., et al., "Adaptive Sampling for Estimating a Scalar Field using a Robotic Boat and a Sensor Network," IEEE International Conference on Robotics and Automation, pp. 3673-3680, Apr. 2007.

* cited by examiner

US 9,464,902 B2

SYMBIOTIC UNMANNED AERIAL VEHICLE AND UNMANNED SURFACE VEHICLE SYSTEM

This invention was made with government support under #1111638, #0916209, #0917676, #0936710 awarded by the National Science Foundation (NSF). The government has certain rights in the invention.

BACKGROUND

Precision agriculture offers to improve crop productivity and farm profitability through improved management of farm inputs, leading to better environmental quality. In precision agriculture, resources such as water, fertilizer and herbicides are only applied to those parts of the field that need them.

A key component of precision agriculture is data collection to determine the current state of the various parts of the field. At present, there are two primary approaches to data collection for precision agriculture: remote sensing and manual data collection. Remote sensing involves collecting information without entering the field. This typically involves using cameras in satellites or aircraft to collect images of the field. Satellite and aerial remote sensing are severely limited by cloud cover and remote sensing from a manned aerial device (either flown by a pilot or radio-controlled by a professional operator) is costly and difficult to plan against weather conditions. Further, soil moisture, crop height, and pest infestations cannot be measured remotely in a vegetated crop. Manual methods involve the collection of data by humans who either gather the data by walking through the field, or guide a vehicle equipped with a sensor through the field. Manual data collection process can be tedious, time-consuming, and expensive.

SUMMARY

A system includes an unmanned aerial vehicle and an unmanned surface vehicle. The unmanned aerial vehicle has a memory storing a plurality of collection points and at least one sensor for collecting sensor data from each of the collection points. The unmanned surface vehicle is capable of moving to a plurality of locations. The unmanned aerial vehicle travels through the air between at least two collection points stored in the memory and the unmanned aerial vehicle is carried between at least two collection points stored in the memory by the unmanned surface vehicle.

In accordance with one embodiment, a method includes storing measurement locations, launching locations, and landing locations in an unmanned surface vehicle's memory and storing image capture locations, launching locations and landing locations in an unmanned aerial vehicle's memory. A data collection routine is initiated during which the unmanned surface vehicle carries the unmanned aerial vehicle between multiple measurement locations and collects sensor data at the multiple measurement locations while the unmanned aerial vehicle is positioned on the unmanned surface vehicle. The unmanned surface vehicle carries the unmanned aerial vehicle to a launching location. The unmanned aerial vehicle launches from the launching location and flies to a plurality of image capture locations. The unmanned surface vehicle travels to a landing location. The unmanned aerial vehicle lands on the unmanned surface vehicle at the landing location.

In accordance with a further embodiment, a method includes identifying a collection of areas in which measurements should be taken, finding a maximal set of non-intersecting areas among the collection of areas and setting an initial tour to a point in each area in the maximal set of non-intersecting areas. A minimum number of sampling locations around each area in the maximal set of non-intersecting areas is then found in order to ensure that there is at least one sampling location in each area of the collection of areas. The initial tour is adjusted to add each sampling location to form an adjusted tour. An unmanned vehicle is then instructed to travel along the adjusted tour and to collect measurements at the point in each area in the maximal set of non-intersecting disks and each sampling location.

DETAILED DESCRIPTION OF ILLUSTRATIVE EMBODIMENTS

Figure 1:
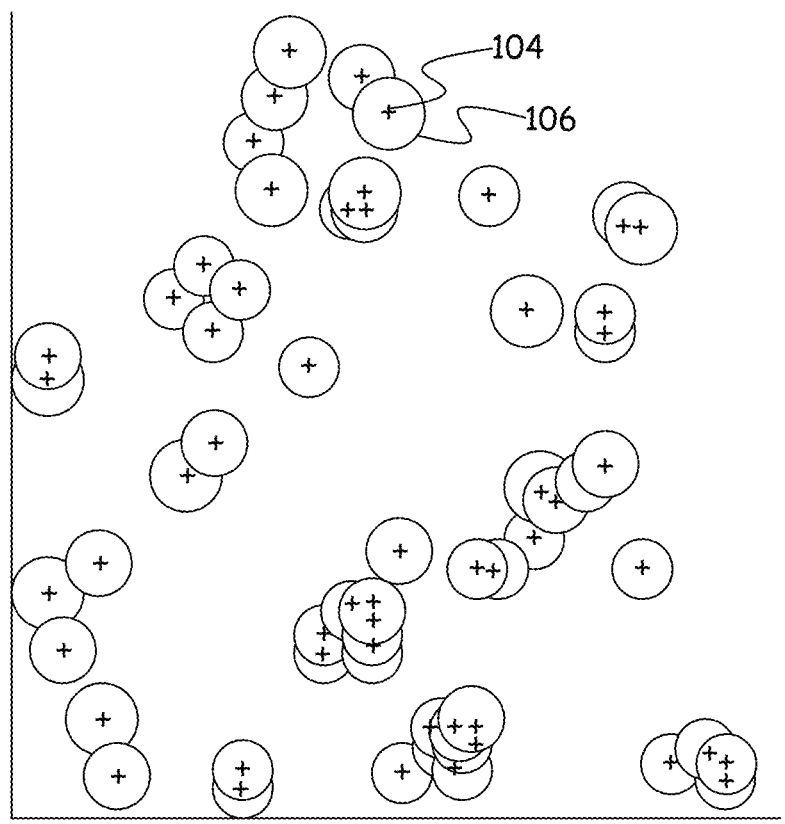
FIG. 1 is a plan view of a geographic area showing a collection of measurement areas associated with PML points.

Embodiments described below provide a low cost Unmanned Aerial Vehicle (UAV) and Unmanned Ground Vehicle (UGV) that work cooperatively to collect data for a precision agriculture application. The system provides multiple on-demand sensing capabilities, and combines the strengths of ground and aerial robots. Ground robots are capable of traveling long distances, carrying large loads and measuring soil data. On the other hand, small aerial vehicles can take images from a low altitude but have limited battery life and the images may need to be complemented with ground measurements. In the embodiments below, a UGV is used to deploy a small, inexpensive UAV at carefully selected measurement locations. As the UAV is taking aerial pictures over a small region, the UGV will take soil measurements. The UAV will then land on the UGV, which will take the UAV to the next deployment location. The ground and aerial measurements collected by the system are used for estimating conditions across a farm field. These estimates in turn guide resource application. The capability to apply the right amount of resources at the right time can drastically reduce resource usage which is desirable from an environmental and economic standpoint.

In accordance with some embodiments, a path is planned for the UAV+UGV system for estimating current conditions in an agriculture field. The method starts with a map of prior conditions of the field (e.g., obtained from satellite imagery). The map classifies each point in the field by assigning a label to the point based on the detected condition of the field at that point. For example, areas can be classified as to the moisture content of the soil as Dry, Moist, Overly Wet or the areas can be classified as to the Nitrogen level in the soil as Low, Medium, or High. After this initial classification, Potentially Mislabeled (PML) points are identified using a probabilistic framework discussed below. A UAV path is planned to visit a maximum number of PML points subject to an energy budget of the UAV where the path includes the ability to have the UAV muled by the UGV between deployment points of the UAV. A UGV path is then planned so that the UGV can take a measurement close enough to each PML point to confirm or reject the classification of the point. This UGV path provides a constant-factor approximation to an ideal path that takes into consideration that the UGV only needs to come within a neighborhood of each point and that there is a cost associated with each measurement the UGV takes. The goal is to minimize the total time spent in traveling and taking measurements. The UAV and UGV are then loaded with the path and sample point information and are released to autonomously traverse the field and collect the desired data.

In more detail, the operating environment is a farm field, which is discretized into a set of points $X=\{x_1, x_2, \ldots, x_n\}$. Each point is assigned an initial label using a prior measurement such as a measurement made using satellite imagery, for example. The current actual condition at each point is not known, however a Gaussian Process is used to estimate the condition of the field at each point from the prior measurements. For each point, the most likely field condition estimate, $N(x)$, is assigned to the point with variance of the estimate as $\sigma(x)$. This most likely field condition estimate is then used to assign a label to each point. For example, each point can be classified using one of three field condition labels: low, medium, and high. These labels can refer to any condition of the field such as moisture content and Nitrogen level, for example. This initial labeling is based on label definitions where each label i is specified by a minimum and maximum condition level, $l_i^-, l_i^+$ respectively. In general, since the true condition levels are unknown and only an estimate of the condition levels is available, it is not certain whether the label for the point is correct. As a result, there is a probability $P_{ij}(x_i)$ that the label j for point $x_i$ is correct where $P_{ij}(x_i)=P(l_j^- \leq N(x_i) < l_j^+)$. The details for computing this probability are given below. Labels are thus assigned to points based on which is most likely to be correct, given the estimates $N(x)$ of each point. The shorter notation $P_l(x_i)$ is used to denote the probability of the most likely label.

Potentially Mislabeled (PML) points are all points in X for which the probability of the most-likely label being correct is below a user-desired value $P_d \in (0, 1)$.

$$X_{pml}=\{x_i \in X: P_l(x_i) \leq p_d\} \quad (1)$$

where $X_{pml}$ is the set of potentially mislabeled (PML) points. The probability of a correct label being assigned to the potentially mislabeled points can be improved by taking soil and aerial measurements near the PML points, as discussed below.

One simple strategy would be to take measurements at every PML point to assign a label with a certainty higher than the user-desired value. However, the ability to take such measurements is constrained because the UAV has a limited battery budget (denoted by B) and the UGV requires some non-zero time (denoted by $C_g$) to take a soil measurement. Thus, the objective is to maximize the number of PML points sampled with the UAV and UGV subject to the UAV's battery constraint and to do so in a minimal amount of time.

The UAV spends some part of its energy budget for each take-off and landing. The average of these energy costs is denoted by $C_a$, so that a combined take-off and landing takes $2C_a$. It is assumed that the UAV and UGV travel at unit speed and the energy required to travel is proportional to the travel time. Hence, distance, time and energy are used interchangeably. Non-unit speeds can be easily accommodated in the analysis. If $\tau_a$ is a set of N deployments for the UAV, then the total cost of the UAV tour is given as $len(\tau_a)+2N \cdot C_a$, where $len(\tau_a)$ is the sum of Euclidean lengths of paths in all deployments. The problem can be concisely stated as, Problem 1 (UAV coverage): Find a UAV tour $\tau_a$ consisting of one or more paths (each of which is associated with a take-off and landing location), to sample the maximum number of PML points, such that the cost of the tour is not greater than the UAV budget.

Given the PML points visited by the UAV, the next objective is to design a UGV path that obtains soil measurements in the least time. The spatial correlation of soil properties means that nearby points are likely to have the same condition level. Hence, as described below, the location of the measurement relative to any PML point should be within a radius defined by the spatial correlation of the measured property. The UGV can thus combine measurement locations for multiple points if their radii overlap. The cost to take measurements is included as an additive time cost $C_g$ for each measurement. The UGV is assumed to have sufficient fuel for the entire trip, but the time cost must be minimized. If $\tau_g$ is a UGV tour with N measurement locations, then the cost of the tour is given as $\text{len}(\tau_g) + N \cdot C_g$. the second optimization problem is then, Problem 2 (UGV cost): Given the set of points visited by the UAV and a radius associated with each point, find a UGV tour of minimum cost that obtains at least one measurement within the radius of each point.

Finding Potentially Mislabeled Points

In this section, points with unacceptably high mislabel probability are found using a map showing condition levels of the points and a Gaussian cumulative distribution function. In particular, points with unacceptably high mislabel probabilities are determined as:

Insert Equations 12 and 13 from New Paper where $\Phi(\ )$ is the Gaussian cumulative distribution function that assumes all points are jointly-Gaussian, with a function K(a, b, θ) to determine the covariance between points a and b, with hyperparameters θ. A prior estimate is required, which in our application is commonly available from a satellite image. Let the points at which prior measurements are obtained be $X_p$, with estimated condition levels $N(X_p)$. Let $\mu_p$ and $\mu_p$ be the mean and variance of the set of prior measurements. The following equations for mean and variance at any specific point are then defined as:

$$N(x_i) = \mu_p + K_\theta(x_i, X_p) K_\theta(X_p, X_p)^{-1}(N(X_p) - \mu_p)$$

$$\sigma(x_i)^2 = \sigma_p^2 - K_\theta(x_i, X_p) K_\theta(X_p, X_p)^{-1} K_\theta(x_i, X_p)^T \quad (2)$$

where $K_\theta(a, b)$ is the covariance function used. Henceforth the squared exponential covariance function is considered, but the method generalizes to other functions as well. Then, $$K_\theta(a, b) = \sigma_f^2 \cdot e^{\left(-\frac{1}{2l^2}\|a-b\|^2\right)} + \delta_{a,b} \sigma_n^2 \quad (3)$$

where $\delta_{a,b} = 1$ if a=b, and zero otherwise. It is assumed the Gaussian Process has been trained, and the hyperparameters $\theta = [l, \sigma_n, \sigma_f]$ are known.

Let $l_j$ be the current label at point $x_i$. Let $\Phi(a)$ be the standard Gaussian Cumulative Distribution Function evaluated at a. Also, define the term $l_j^*(x_i)$ to be the "closest" labeling threshold, for each label, to the current estimate at point $x_i$ as follows, $$l_j^*(x_i) = \min(|N(x_i) - l_j^-|, |N(x_i) - l_j^+|) \quad (4)$$

Due to the Gaussian noise assumption, an upper bound on the probability the point is mislabeled is found as follows:

A point $x_i$, with label $l_j$ has a likelihood of being mislabeled $P_{mislabeled}$, which satisfies, $$P_{mislabeled}(x_i) \leq 2 \cdot \Phi\left(\frac{-l_j^*(x_i)}{\sigma(x_i)}\right) \quad (5)$$

where $l_j^*(x_i)$ is defined as the closest labeling boundary to $N(x_i)$.

Thus, the mislabel probability is a function of both the current estimate $N(x_i)$ and the variance $\sigma(x_i)$. Of these quantities, $\sigma(x_i)$ can be controlled since it depends on the distance from the measurement location to point $x_i$. Specifically, in order to reach a desired probability threshold $P_d$, the measurement location should be chosen so that the variance is:

$$\sigma(x_i) \leq \frac{l_j^*}{\Phi^{-1}\left(\frac{P_d}{2}\right)} \quad (6)$$

Using the spatial correlation from Equation 2, the squared covariance function of Equation 3, and a single is a measurement point z using a Sensor S with measurement error $\sigma_s$ such that $\sigma^2(z) = \sigma_s^2 = \sigma_n^2$, the relationship between the measurement location and the variance at $x_i$ can be determined as:

$$\sigma^2(x_i | z) = \sigma^2(z) - K(x_i, z)[K(z, z)]^{-1} K(x_i, z)^T \quad (7)$$

$$\sigma^2(x_i | z) = \sigma_s^2 - \frac{\sigma_f^2 \cdot e^{\left(-\frac{1}{l^2}\|a-b\|^2\right)}}{\sigma_f^2 + \sigma_s^2} \quad (8)$$

Setting the right hand side of equation 6 as $\sigma_d^2$, equations 6 and 8 can be combined as:

$$\sigma_d^2 \geq \sigma^2(x_i | z) = \sigma_s^2 - \frac{\sigma_f^2 \cdot e^{\left(-\frac{1}{l^2}\|a-b\|^2\right)}}{\sigma_f^2 + \sigma_s^2} \quad (9)$$

or $$\sigma_d^2 \geq \sigma_s^2 - \frac{\sigma_f^2 \cdot e^{\left(-\frac{1}{l^2}\|a-b\|^2\right)}}{\sigma_f^2 + \sigma_s^2} \quad (10)$$

Solving equation 10 for the distance between the measurement point and xi gives:

$$\|z - x_i\|^2 \leq -l^2 \log_e[(\sigma_s^2 - \sigma_d^2)(\sigma_f^2 + \sigma_s^2)\sigma_f^{-4})] \quad (11)$$

$$\|z - x_i\|^2 \leq \quad (12)$$
$$-l^2 \log_e\left[\left(\sigma_s^2 - \frac{\min(|N(x_i) - l_j^-|, |N(x_i) - l_j^+|)}{\Phi^{-1}\left(\frac{P_d}{2}\right)}\right)(\sigma_f^2 + \sigma_s^2)\sigma_f^{-4}\right]$$

Thus, for every PML point $x_i$, a radius $\|z - x_i\|^2$ can be determined that is a function of the probability threshold $P_d$ and the distance between the measured condition level at point $x_i$, $N(x_i)$ to the closest label boundary where the radius sets a maximum distance from the point, as a function of the sensor noise and current uncertainty, from which a sample must be obtained such that the label currently assigned to the point $x_i$ has a probability greater than the probability threshold $P_d$ of being correct.

FIG. 1 provides an example of a geographic area showing PML points as crosses such as cross 104 and the area where a measurement is to be taken is depicted as a disk with the radius determined above centered on the PML point such as disk 106. For each point, a measurement from inside the respective disk will indicate that the label assigned to the PML point is correct with a probability greater than the probability threshold $P_d$.

Path Optimization

In this section, a method is described for finding the UAV+UGV tours to visit the most number of PML points subject to the UAV battery budget. The method operates in two phases: first the subset of PML points to be visited by the UAV is found and then the tour (i.e. order and sampling locations) for the UGV is found. The tour for the UGV also includes take-off and landing locations for the UAV.

A. Computing the UAV Tour

The method of finding the maximum subset of PML points to be visited by the UAV begins with a graph $G(V, E, \pi, w)$ with weights ($w(u, v)$) on edges, and rewards $\pi(v)$ on the vertices. The objective is to find a tour of a subset of vertices collecting maximum reward, with the constraint that the sum of weights of edges on the tour is less than a given budget.

First consider the simpler case of finding the maximum subset of points in a UAV-only system. For simplicity, let the camera footprint be a single point for now. The UAV tour will consist of a single path with one take-off and landing location. A graph is built with PML points as the vertices. An edge is added to G between every pair of points with weight equal to the Euclidean distance between the points. Each vertex is given a unit reward. The budget for the UAV equals the battery lifetime minus $2C_a$ to account for the single takeoff and landing. The method then finds the path that traverses the most PML points while having a length that is less than or equal to the available travel budget for the UAV.

Since the edge weights are Euclidean distances, this graph is a complete metric graph. Blum et al., "Approximation algorithms for orienteering and discounted-reward tsp", SIAM Journal on Computing, vol. 37, no. 2, PP. 653-670, 2007 presented a 4-approximation for orienteering problems on undirected metric graphs. Applying this algorithm to the graph constructed above will yield a UAV tour visiting at least ¼th of the PML points visited by the optimal algorithm.

Now consider the case of a UAV+UGV system. The UGV can transport the UAV between two PML locations, without affecting the UAV's battery life. To account for this movement, the edge weights are modified accordingly. Furthermore, since the UAV carries a camera with a footprint of diameter C, it can sample a point without flying directly over it. Hence, the set of vertices should also be modified. The detailed construction of the input graph then becomes:

(1) Create a square grid of resolution $C/\sqrt{2}$ over the plane representing the field. Each point in $X_{pml}$ is associated with its nearest grid location. Store the number (denoted by $\pi(v)$) of PML points associated with a grid location. For example, in FIG. 2(*a*) the grid is shown by horizontal and vertical lines such as horizontal line 200 and vertical line 202. In each box formed by the horizontal and vertical lines that contains at least one PML point, the number of PML points in the box is assigned as the vertex weight $\pi(v)$. For example, box 206 contains two PML points 208 and 210 and is assigned a vertex weight of 2.

(2) Let V be the set of grid vertices with at least one PML point. For each vertex $v \in V$, let $\pi(v)$ be the number of associated PML points.

(3) Build a complete undirected graph $G=[V,E,\pi,w]$. For each edge between $(u, v) \in V$, add a weight $w(u, v)=\min\{d(u, v), 2C_a\}$. This implies there are two types of edges between grid points: The UAV can either use the UGV to travel paying only for the ascent/descent ($2C_A$) or travel directly between points paying the distance cost ($d(u, v)$).

(4) Find the path through the graph that provides the highest total vertex weight formed by summing the vertex weight of each grid visited by the UAV while having a total edge cost equal to the sum of the costs of each edge the UAV travels along that is less than the budget for the UAV.

G is a metric graph. Consider a triple of vertices u, v, w. We know $w(u, v), w(v,w), w(w, u) \leq 2C_a$. It is easy to see the triangle inequality holds when two or three edges have weights equal to $2C_a$. Consider the case when only one edge has weight equal to $2C_a$, say $w(u, v)=2C_a$. Now, $w(v,w)+w(w, u)=d(v,w)+d(w, u) \geq d(u, v)$. Since $w(u, v)=\min\{2C_a, d(u, v)\}=2C_a$, we have $d(u, v) \geq 2C_a$. Hence, $w(v,w)+w(w, u) \geq w(u, v)$. And since $w(u, v)=2C_a$ and $w(v,w), w(w, u)<2C_a$, $w(u, v)+w(w, u) \geq w(v,w)$ and $w(u, v)+w(v,w) \geq w(w, u)$. For the case when all three edges have weights less than $2C_a$, the weights are equal to Euclidean distances. Hence, weights satisfy triangle inequality in addition to symmetry, identity and non-negativity. Hence, the graph constructed above is a complete metric graph. As a result, the 4-approximation of Blum mentioned above may be used to find an approximation to the optimal path for the UAV.

An example of a UAV tour identified using the method above is shown in FIG. 2(*b*). In FIG. 2(*b*), a two airborne paths 220 and 222 are shown as dotted lines while a ground path 224 is shown as a solid line. For airborne path 220, the UAV launches at location 226 and lands on the UGV at location 228. The UAV is then muled or carried by the UGV along ground path 224. When the UGV reaches location 230, the UAV launches again and travels along airborne path 222 before landing again on the UGV at point 232.

As shown in FIG. 2(*b*), the UAV tour is not always able to visit all of the PML points due to the battery budget of the UAV. For example, the set of PML points 234 and the set of PML points 236 are not sampled by the UAV.

B. Computing the UGV Tour

The method in the previous subsection gives the subset of PML points to be sampled by the UAV and thus by the UGV as well. The second part of the method involves constructing a minimum cost tour for the UGV to visit each point in the subset. Note, for each PML point sampled by the UAV, the UGV must take a sample within the disk defined above. Thus, a tour must be found in which the UGV visits all disks of the PML points sampled by the UAV and takes a measurement within each disk.

The problem of finding the best tour for the UGV differs from the problem of finding a best route for a Traveling Salesperson to visit a set of equally-sized Neighborhoods because unlike the Traveling Salesperson with Neighborhoods problem, the problem of finding the best tour for the UGV must take into account the time required for the UGV to take a measurement in each disk. Thus the UGV must choose a measurement location within each disk such that the length of the tour and the number of distinct measurement locations are minimized. Specifically, finding the minimum cost UGV tour involves:

Given a set of disks with uniform radius r and centers at points X, find a tour $\tau$ of N distinct sample locations to minimize the cost $\text{len}(\tau)+C \cdot N$ such that each disk contains a sample location, where C is a time cost for taking a measurement and $\text{len}(\tau)$ is the time needed to move along the path of the tour.

The first step in determining the UGV path is to identify a Maximal Independent Set (MIS) of non-intersecting disks, from the set of disks for the PML points sampled by the UAV. The MIS consists of the largest number of disks that can be found that do not overlap any other disks in the MIS. A disk can overlap other disks for the PML points and still be in the MIS. However, none of the disks in the MIS overlap another disk in the MIS.

Figure 2A:
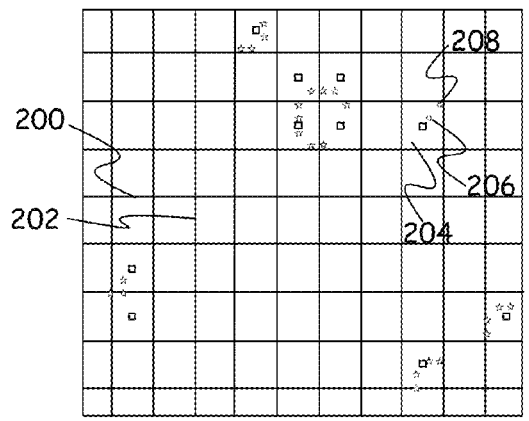
FIG. 2(a) is a plan view of a geographic area divided into grids showing a collection of PML points.
Figure 2B:
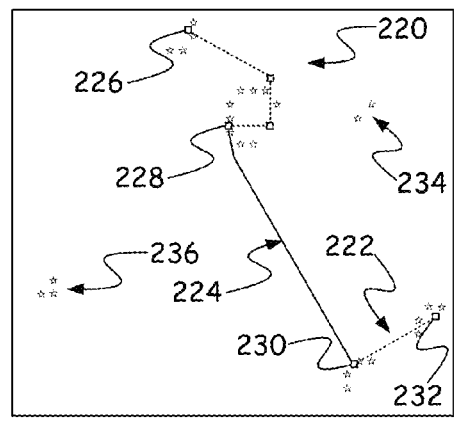
FIG. 2(b) is a plan view of the geographic area of FIG. 2(a) showing a combined aerial and surface tour for an unmanned aerial vehicle to capture image data of PML points.
Figure 2C:
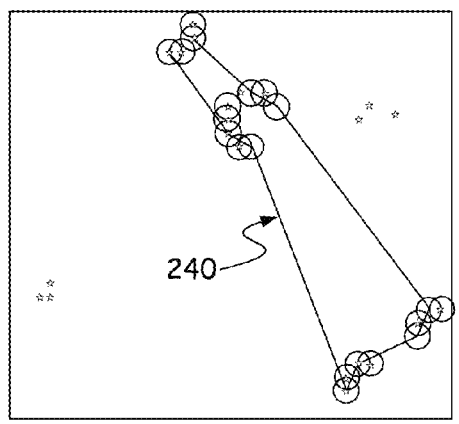
FIG. 2(c) is a plan view of the geographic area of FIG. 2(a) showing an initial tour for an unmanned surface vehicle to visit the center of a Maximal number of non-intersecting sampling areas around the PML points sampled by the unmanned aerial vehicle.

Next, a lowest cost tour is found to visit the center of each disk in the MIS. This tour is based only on the travel time needed to travel between disk centers. This tour intersects the circumference of each disk in the MIS twice. An example of an MIS tour 240 for the PML points of FIG. 2(b) is shown in FIG. 2(c).

After the tour of to the center of the MIS disks has been established, it must be modified to ensure that each disk that intersects a MIS disk is also visited. One simple way to do this would be to start from an arbitrary disk in the MIS, follow the tour in the clockwise order up to the intersection point of the next disk, then follow the circumference of this disk in the clockwise order up to the second intersection point of the same disk. This continues until the starting point is encountered again. The process is then repeated in the anti-clockwise direction.

Figure 3A:
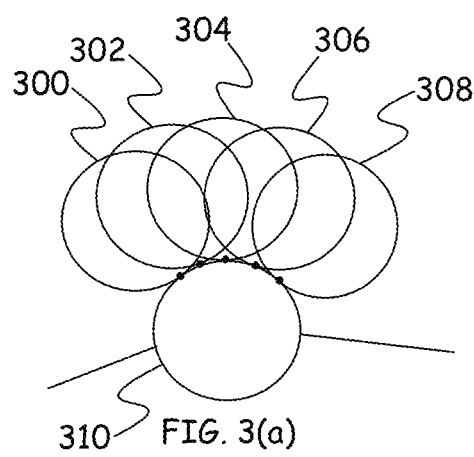
FIG. 3(a) shows a non-ideal collection of sampling locations that would be formed using a simple solution to the Traveling Salesperson with Neighborhood problem.

This algorithm ensures that the tour intersects all disks by moving along the circumference of each disk in the MIS. However, when the UGV has to stop and obtain a measurement in each disk, restricting the motion to the circumference can be potentially costly in terms of the number of measurements. For example, consider the situation shown in FIG. 3(a) where the outer disks 300, 302, 304, 306, and 308 intersect with each other only outside the circumference of a disk 310 in the MIS. Since the tour in the standard algorithm only moves along the circumference, it will be forced to take one measurement for every outer disk, which can be as large as O(n), whereas the optimal algorithm can visit a small number of intersection points, not necessarily on the circumference of an MIS disk.

In accordance with one embodiment, the method above is modified in order to simultaneously find sampling locations for the tour. The additional length due to this new local strategy and the number of samples obtained with respect to the optimal are both bound. In accordance with this embodiment:

(1) Starting from an arbitrary point, follow the tour of the centers of disks in the MIS (FIG. 2(c)).

Figure 3B:
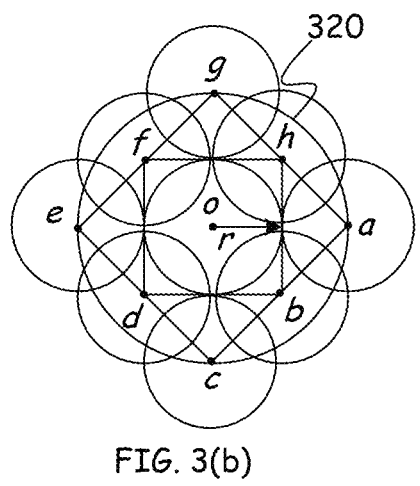
FIG. 3(b) shows a collection of sampling locations around a non-intersecting sampling area of a PML point under one embodiment.

(2) When a new center (say o) is reached on the tour, before visiting the next center on the tour, first visit the eight sites as shown in FIG. 3(b) where o is the center of the disk in the MIS, sites b, d, h, f lie on a square of side $2\sqrt{2}r$ centered at o, and sites a, c, e, g lie on a square of side $2\sqrt{2}r$ rotated by $$\frac{\pi}{4}.$$

Figure 2D:
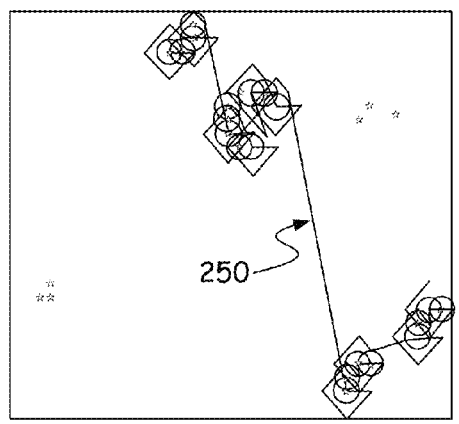
FIG. 2(d) is a plan view of the geographic area of FIG. 2(a) showing an adjusted tour for an unmanned surface vehicle to visit the sampling areas around all of the PML points sampled by the unmanned aerial vehicle.

After visiting the last of these sites, continue toward the center of the next disk in the MIS. The resulting tour 250 for the MIS of FIG. 2(c) is shown in FIG. 2(d).

(3) Restrict the candidate sampling locations to the set of centers of disks in MIS and the set of eight sites as described above. Denote this set of candidate sampling locations by S.

It can be shown that the set S defined above intersects all disks in X by letting S be the set of all centers of the disks in a MIS of non-overlapping disks X of radius r. Let S also contain the eight sites as described above. Then, for each disk in X, there exists a point in S lying in its interior.

This can be proven by considering FIG. 3(b) where o is the center of the disk in the MIS. Then all disks that intersect the disk at o, lie within a disk of radius 2r from o. This outer disk 320 may be denoted as $D_2$. Let $S_o = \{o, a, \ldots, h\}$. We can observe that the set of disks of radius r centered at all sites in $S_o$ form a cover of $D_2$. Hence, any point in $D_2$ is at a distance of at most r from a site in $S_o$. Now consider any disk centered at o' that intersects the disk centered at o. $o' \in D_2$, hence there exists a site in $S_o$ at a distance r from o', i.e., lying within the disk at o'.

The size of S is bound with respect to the size of the optimal number of samples N*. In particular, if N* is the number of samples taken by an optimal algorithm, then $|S| \leq 9N^*$. This follows from the fact that S contains 9 sites per disk in an MIS of nonintersecting disks: one for the center, and eight lying on the two squares as shown in FIG. 3(b). Hence, $|S| = 9|MIS|$. No two disks in the MIS overlap, hence they cannot share any sampling location between them. Hence, the optimal number of samples must be larger than the number of disks in the MIS or $N^* > |MIS|$ and thus $|S| \leq 9N^*$.

The length of the tour using the method above is also bound and is no more than a constant times the length of the tour of an optimal algorithm for sampling the disks. Specifically, let $T_{ALG}$ be the tour constructed by the method above, and T* be the tour for the optimal sampling algorithm. Then $\text{len}(T_{ALG}) \leq 44T^*$. For ease of notation, both a tour and its length are referred to by T, and T* refers to an optimal tour.

Denote by $T_I$ and $T_C$ the Traveling Sales Person with Neighborhoods tour of the MIS and the Traveling Sales Person tour of the center of the MIS respectively. Let n be the total number of input disks where $$n \leq \left(4 + \frac{4T^*}{\pi r}\right).$$

Now $$T_C^* \leq T_I^* + 2nr$$

$$T_C^* \leq T^* + 2nr$$

$$T_C^* \leq T^* + 8r + \frac{8T^*}{\pi}$$

$$T_C^* = T^*\left(1 + \frac{8}{\pi}\right) + 8r$$

The first inequality follows from the fact that a tour of the centers can be constructed by taking a detour of at most 2r for each disk from the tour of the disks. The second inequality comes from the fact that the optimal tour is also a tour of the disks in the MIS. $T_{ALG}$ consists of a TSP tour of the centers of the disks in MIS and a tour of the regular hexagon surrounding each disk. Using a $(1+\epsilon)$-approximation for the Traveling Sales Person tour, we get $$T_{ALG} \leq (1+\epsilon)T_C^* + \sqrt{2}\,nr + 7\sqrt{2}\,nr$$

$$T_{ALG} \leq (1+\epsilon)\left(\left(1 + \frac{8}{\pi}\right)T_I^* + 8r\right) + 32\sqrt{2}\,r + \frac{32\sqrt{2}\,T_I^*}{\pi}$$

The $\sqrt{2}nr$ term in the first inequality comes from the part of moving from the center of the disk in MIS to the closest of the eight sites (from o to h in FIG. 3(b)). The $7\sqrt{2}nr$ comes from visiting each of the eight sites (starting from h through a in FIG. 3(b)).

The length of any path that visits three non-overlapping disks of radius r is at least 0.4786r. Thus when the MIS contains more than 3 disks, we get $T^* \geq 0.4786r$. Therefore, $$T_{ALG} \leq T^* \left[ (1+\epsilon)\left(1+\frac{8}{\pi}\right) + \frac{32\sqrt{2}}{\pi} + 0.47(8+32\sqrt{2}+8\epsilon) \right] \leq 44T^*$$

for small E.

The total cost of the method above is then bound by the cost of an optimal sampling algorithm. Specifically, let C* be the cost of the optimal algorithm for sampling the disks. Therefore, $C^* \geq len(\tau^*) + N^* \cdot C_g$ where $\tau^*$ is the optimal tour visiting all disks, and N* is the minimum number of sample locations such that each disk has at least one sample location.

The cost $C_{ALG}$ of the method described above is:

$$C_{ALG} = len(\tau) + N \cdot C_g, \leq 44len(\tau^*) + 9N^* \cdot C_g, \cdot \leq 44C^*.$$

Figure 2E:
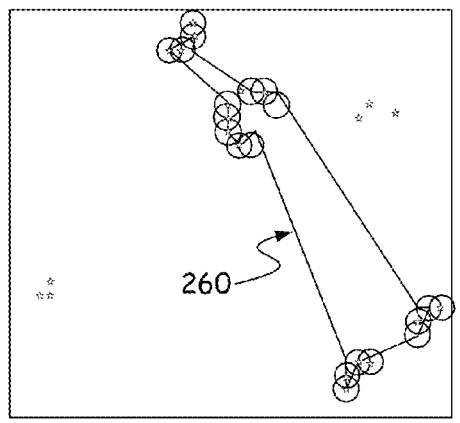
FIG. 2(e) is a plan view of the geographic area of FIG. 2(a) showing a further adjusted tour in which sampling locations that are outside of a sampling area around a PML point have been removed from the tour shown in FIG. 2(d).
Figure 2F:
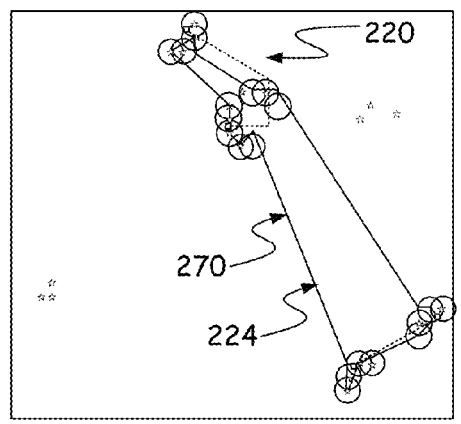
FIG. 2(f) shows a plan view of the geographic area of FIG. 2(a) showing a final combined tour for an unmanned surface vehicle and unmanned aerial vehicle system.

In practice, all nine sites around an MIS disk do not have to be sampled. Sample locations that do not intersect any disk are discarded from the sampling set or a smaller subset that samples all the disks is found by applying a greedy algorithm that selects sample points that intersect more disks over sample points that sample fewer disks. Then, a tour 260 of just these sampling locations is found, as shown in FIG. 2(e). Nest, take-off and landing locations for the UAV are added to S if those locations differ from the sampling locations. This produces the final tour 270 for the UGV combined with the AUV tour 220, 222 and 224 as shown in FIG. 2(f). After visiting a take-off location, the UGV continues along its tour. Whenever, the time to reach a landing location from the current position of the UGV tour becomes equal to the landing time of the UAV, the UGV can deviate from its pre-planned route, visit the landing location, and return to its pre-planned route. The total distance overhead for the UGV is at most the budget of the UAV and in practice, not very significant.

In a second embodiment, after determining the tour to the MIS disk centers, the UGV tour is determined using a geometric hitting method.

Before presenting this second embodiment, consider the following straight-forward approach for finding the set of candidate sampling locations. Draw a square grid with side $r_{min}$ about each disk in the MIS. Extend the grid so that any disk that intersects with a disk in the MIS lies within the grid. Now add a local detour to the tour of the MIS disk centers, $T_C$, such that every time a new disk in the MIS is visited, a sample is obtained at all of the extended grid locations near this disk. This guarantees that a sample will be obtained for each of the input disk in X. However, the number of grid locations will be $$O\left(\frac{r_{max}^2}{r_{min}^2}\right)$$

per disk in the MIS. On the other hand, there could possibly be a single location within each MIS disk, where an optimal algorithm can obtain a sample. Thus, this approach would yield an $$O\left(\frac{r_{max}^2}{r_{min}^2}\right)$$

approximation with respect to the number of measurements. Instead, the following procedure will obtain a constant factor approximation with respect to the number of measurements, and guarantee an overall $$O\left(\frac{r_{max}^2}{r_{min}^2}\right)$$

approximation for an optimum sampling algorithm that obtains a sample from each disk.

After finding the tour of the centers of the MIS disks, the smallest sized set of points is found, such that there exists at least one point in the interior of every disk in X. Consider the arrangement of disks in X in the plane. A set of points P is created by placing a point in each disk in the arrangement. For each point $p \in P$, let R be the set of disks containing p. Let $\mathcal{R}$ be the set of such sets for all points in P. A geometric hitting set problem is then solved for the set system $(P, \mathcal{R})$. The hitting set solution finds the minimum number of points in P such that each disk in X has at least one such point in its interior. Finding the minimum number of points is NP-complete in general. However, there exist efficient approximation algorithms, e.g., $(1+\epsilon)$-approximation in N. H. Mustafa and S. Ray, "Improved results on geometric hitting set problems," Discrete & Computational Geometry, vol. 44, no. 4, pp. 883-895, 2010, that can be used. Let C be the result from the hitting set algorithm.

Instead of visiting a point in C, however, a grid is imposed and grid points are visited that neighbor a point in C. This allows the length of the tour to be bounded, while simultaneously bounding the number of measurements.

Let x be some center along the tour $T_C$. Let $N(x) \subset C$ be the set of all candidate locations corresponding to disks in X whose centers are at most $2r_{max}$ from x. These are disks that are completely contained inside a disk of radius $3r_{max}$ centered at x.

Let $p \in N(x)$ be any such candidate location. A grid of resolution $r_{min}$ is imposed over the entire plane. Let G(p) be the set of all grid points within distance $2r_{min}$ from p. There are at most 25 such grid points. Any disk having radius greater than $r_{min}$ that contains p must contain at least one grid point in G(p). Hence, the samples can be restricted to only grid points G(p) without missing any disks.

The final tour is obtained by modifying the tour of the MIS centers as follows. After having visited center x, instead of continuing on to the next center, the tour visits the set of all grid points within a distance of $3r_{max}$ of x. Along this tour, a sampling location is added every time a grid point belonging to G(p) for some $p \in N(x)$ is encountered. Let S be the set of all sampling locations.

In general, S contains more sampling locations than necessary. As post-processing, the method greedily chooses a smaller subset of S such that each disk contains one sampling location. Having found this subset, the tour is just these locations. The construction described above allows the performance of the algorithm to be conveniently bound.

The correctness of the algorithm is shown by proving that S has at least one sampling location in each input disk (not just the larger disk). Let S be the set of all candidate sampling locations found by the method above. The set S of sampling locations is computed based on the solution C to the hitting set problem. For any disk in X centered at x, there exists a point p∈C lying in its interior. Since the sampling locations are chosen from the grid, the method above may not be able to choose p. However, by including at most 25 points for each point in the hitting set, all of the disks that intersect the disk centered at x will be contain one of the 25 sample points.

Specifically, G(p) is the set of grid points within $2r_{min}$ of p. Instead of sampling at p, we sample at some grid point in G(p). Let D be any disk in X that contains p. At least one grid point, say p'∈G(p), is also contained in D. Draw a disk D2 centered at p, with radius $2r_{min}$. Any disk of radius $r_{min}$ contained completely within D2 must also contain at least one point of G($_p$). Replace D by a smaller disk, say D1, such that D1 has a radius $r_{min}$, D1 is contained completely within D, and D1 contains p. D1 is completely contained within D2. Hence, D1 contains some point of G(p).

Next, it is possible to show that this point p' is also included in S. There are one of two cases: either the larger disk centered at x lies in the MIS or not. If it lies in the MIS, then p' is within $3r_{max}$ of x and we are done. If not, then the larger disk of radius $r_{max}$ intersects some other larger disk, centered at say x', lying in the MIS. Hence, the distance between x and x' is at most $2r_{max}$, which implies that p' is at most $3r_{max}$ away from x'. Hence, in both cases, p' will be in S.

The method above provides an upper bound on the number of candidate sampling locations. Specifically, if N* is the number of samples collected by an optimal method of sampling the disks, and S is the set of sample locations determined using the method above, then |S|≤25(1+ε)N*. This is proven by assuming that N* is the minimum number of sampling points, such that there exists at least one sampling point per disk in X. The set C can be found using any constant-factor approximation for the hitting set problem. Under one such approximation, |C|≤(1+ε)N*. For each point in C, at most 25 grid sampling points are added to S. Hence, |S|≤25(1+ε)N*.

The total distance traveled during the tour determined using the geometric hitting method is also bound. Let $T_{ALG}$ be the tour constructed using the geometric hitting method, and T* be the tour for the optimal sampling algorithm. Then $$len(T_{ALG}) \le O\left(\frac{r_{max}^2}{r_{min}^2}\right)T^*.$$

For ease of notation, both a tour and its length are referred to by T, and T* refers to an optimal tour.

Denote by $T_I$ and $T_C$ the Traveling Sales Person with Neighborhoods tour of the MIS and the Traveling Sales Person tour of the center of the MIS respectively. Let n be the total number of input disks. Now $$T_C^* \le T_I^* + 2nr$$

$$T_C^* \le T^* + 2nr$$

The first inequality follows from the fact that a tour of the centers can be constructed by taking a detour of at most $2r_{max}$ for each disk from the tour of the disks. The second inequality comes from the fact that the optimal tour is also a tour of the disks in the MIS.

$T_{ALG}$ consists of a Traveling Sales Person tour of the centers of the disks in MIS and a tour of the grid locations within $3r_{max}$ of the center. Using a (1+ε)-approximation for the Traveling Sales Person tour:

$$T_{ALG} \le (1+\epsilon)T_C^* + 36n\frac{r_{max}}{r_{min}}r_{max} + 6n(1+\sqrt{2})r_{max}$$

Here, $$6\frac{r_{max}}{r_{min}}$$

are the number of horizontal rows in the grid traversed, each horizontal row has a length of $6r_{max}$. The last term accounts for moving from the center of the disk to the start and end of the grid, and moving vertically along one column.

The length of any tour that visits n non-overlapping disks of radius $r_{max}$ is at least $$\frac{n}{2}0.4786r_{max}.$$

That is $$T^* \ge \frac{n}{2}0.4786r_{max}.$$

This gives, $$\frac{2}{0.4786}T^* \ge nr_{max}.$$

Therefore, $$T_{ALG} \le (1+\epsilon)(T^* + 2nr_{max}) + \left(36\frac{r_{max}}{r_{min}} + 6 + 6\sqrt{2}\right)nr_{max}$$

$$T_{ALG} \le (1+\epsilon)T^* + \left(36\frac{r_{max}}{r_{min}} + O(1)\right)nr_{max}$$

$$T_{ALG} \le O\left(\frac{r_{max}}{r_{min}}\right)T^*$$

where $r_{max}$ and $r_{min}$ are the radii of the largest and the smallest of the disks in X, respectively.

In addition, the total cost of the sampling tour of the geometric hitting method, including both the tour length and the cost of sampling, is bounded. Let C* be the cost of the optimal algorithm for sampling the disks in X. Therefore, C*≥T*+N*·$C_g$ where T* is the optimal tour visiting all disks, and N* is the minimum number of sample locations such that each disk has at least one sample location.

The cost $C_{ALG}$ of the sampling tour formed through the geometric hitting method is:

$$C_{ALG} = T_{ALG} + |S| \cdot C_g, \ \leq O\left(\frac{r_{max}}{r_{min}}\right)T^* + O(1)N^* \cdot C_g, \ \cdot \leq O\left(\frac{r_{max}}{r_{min}}\right)C^*.$$

Simulations were performed to confirm that the symbiotic UGV+UAV system is able to sample more PML points than the UAV alone. To generate realistic data for the simulations, a generative model of Nitrogen levels based on actual data taken from a field and realistic values for the sampling noise for both systems were used. The data consists of 1375 soil measurements taken manually in a 50 m by 250 m corn field, along with corresponding 1 m spatial resolution remote sensing images in the green (G), red (R) and near infrared (NIR) portions of the spectrum. The samples were taken along a dense uniform coverage and provided the levels of soil organic matter (OM). R and NIR are known to be inversely related to crop Nitrogen status.

Organic Matter (OM) was used as a proxy for the initial quantity of soil Nitrogen supplied to the crop. The UGV was modeled as taking direct measurements of OM, corrupted by some sensor noise $\sigma_g$, and the UAV as measuring the Normalized Difference Vegetation Index (NDVI), which is a combination of NIR and R levels. We assume the NDVI levels are corrupted by sensor noise $\sigma_a$. The noise variances were estimated to be $\sigma_a=0.31$ and $\sigma_g=0.5$ for our dataset, using the following procedure.

To model the spatial patterns of the OM levels, we used Gaussian Process (GP) regression over the set of sample points and OM measurement values. This densely-sampled GP defined the hyperparameters which were used to generate new ground-truth Nitrogen maps in the simulations.

As part of the ground-truth GP regression, it is possible to estimate the sample noise ($\sigma_n$ and $\sigma_s$ above) at each point from the data directly. This value is used directly as $\sigma_g$, since it is assumed that the robot would have the same sensing capability as the human operators. To estimate $\sigma_a$, the sample covariance between NDVI (from the hand-measured R and NIR levels) and OM (measured directly) can be calculated, yielding a $$2 \times 2 \text{ matrix}, \begin{bmatrix} \sigma^2_{OM} & \sigma^2_{OM,NDVI} \\ \sigma^2_{NDVI,OM} & \sigma^2_{NDVI} \end{bmatrix}.$$

From this, the variance in OM given a measurement of NDVI can be found as $$\sigma^2_a = \sigma^2_{OM|NDVI} = \sigma^2_{NDVI} - \frac{\sigma^2_{OM,NDVI}}{\sigma^2_{OM}}.$$

For the simulations, a prior estimate of OM levels was formed by down sampling each randomly-generated ground truth N-map by a factor of 20 and fitting a new GP. From this prior GP, the PML point set is found as discussed above. For the simulation, 100 N-maps for a 600×400 m field were generated and PML points were found on each map using a desired labeling probability of 0.6. The number of PML points in any instance depends on the randomly generated map.

Results

The procedures described above for identifying a UAV path were used to find the subset of PML points visited by the UAV only and the UAV+UGV system, subject to a battery constraint of 25 minutes.

Figure 4B:
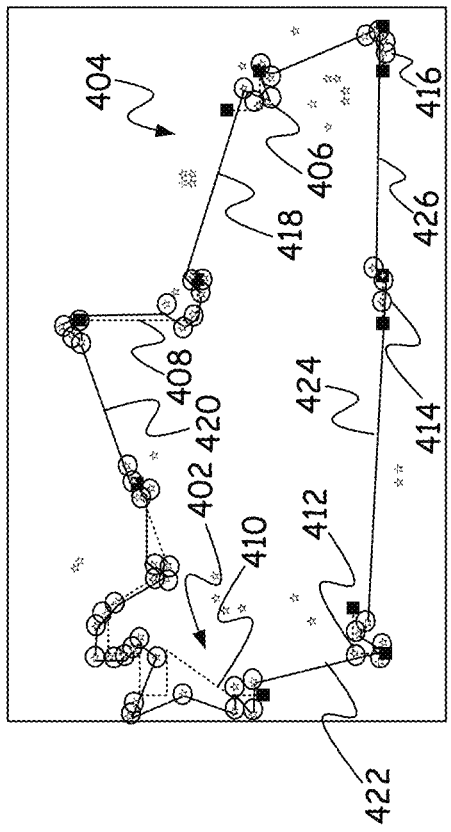
FIG. 4(b) shows a plan view of the geographic area of FIG. 4(a) showing combined tours for an unmanned aerial vehicle and unmanned surface vehicle in accordance with one embodiment.
Figure 4D:
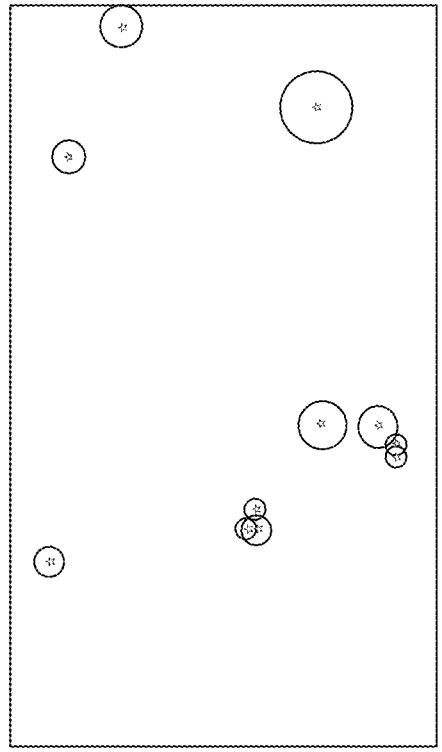
FIG. 4(d) shows a plan view of the geographic area of FIG. 4(a) showing the PML sampling areas that are not sampled using a combined unmanned aerial vehicle and unmanned surface vehicle system.
Figure 4A:
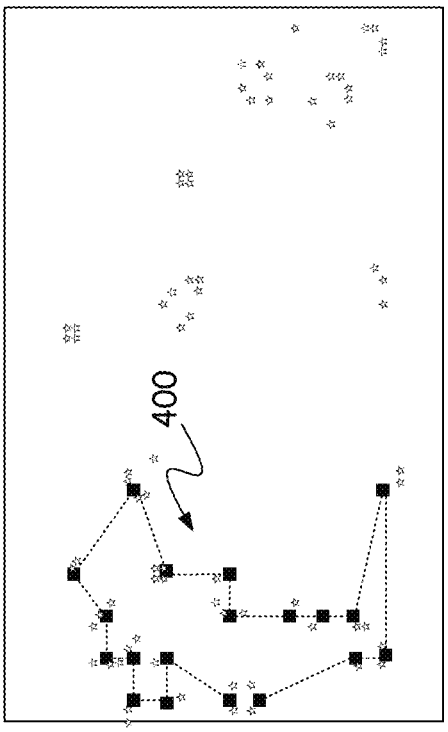
FIG. 4(a) shows a plan view of a geographic area showing a tour identified for a system that uses only an unmanned aerial vehicle.
Figure 5:
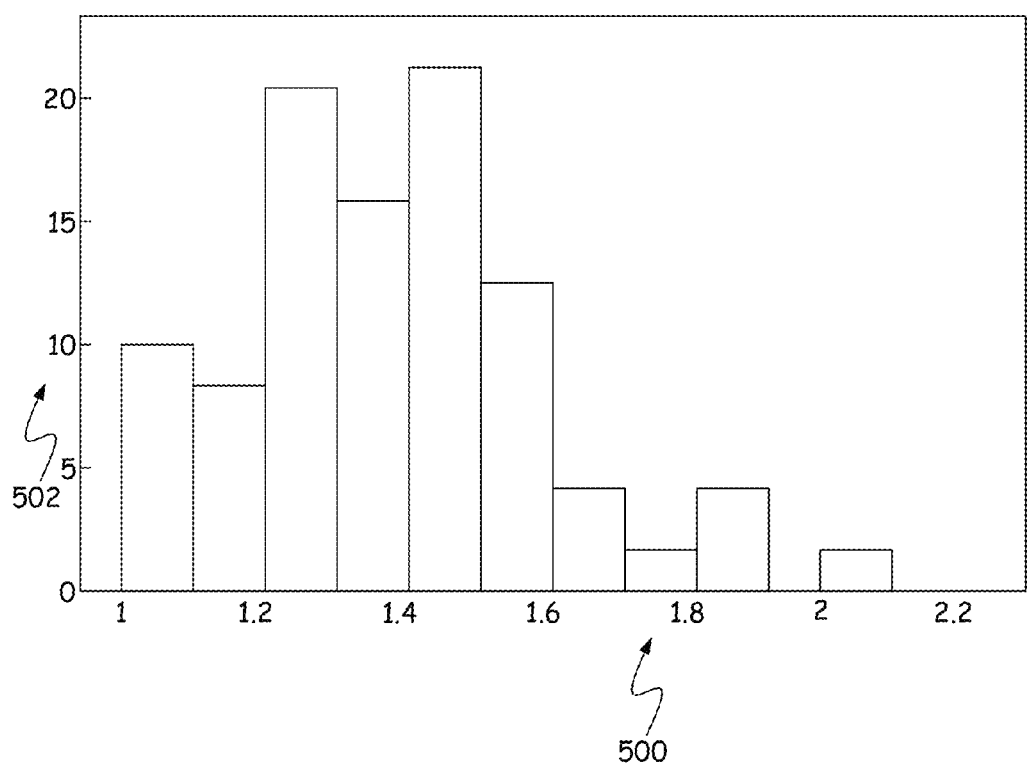
FIG. 5 provides a graph of the ratio of PML points visited by an unmanned aerial vehicle and unmanned surface vehicle system over PML points visited by an unmanned aerial vehicle alone.

FIG. 4(a) shows a tour 400 for a system that only uses a UAV for one of the simulated fields. FIG. 4(b) shows a UAV path 402 and a UGV path 404 for a UAV+UGV system. UAV path 402 includes airborne portions 406, 408, 410, 412, 414, and 416, shown dashed lines, and muled or carried portions 418, 420, 422, 424, and 426, shown as solid lines. During the muled or carried portions, the UAV is carried on the UGV. Comparing FIG. 4(a) to FIG. 4(b) it can be observed that the UAV-only tour is constrained to only one part of the field, whereas the UAV+UGV system can obtain measurements from more locations. This input instance consisted of 75 potentially mislabeled points, with the UAV-only tour covering 38 points and the UAV+UGV tour covering 50 points. FIG. 5 shows a histogram of the ratio of the points covered by the UAV+UGV and the UAV-only tours for 100 random instances with ratio values shown along horizontal axis 500 and the number random instances having each ratio shown on vertical axis 502. As expected, the ratio is always greater than 1 as the UAV+UGV system is at least as good as a UAV-only system in terms of the number of points visited Table I shows the effect of varying the budget on the percentage of input PML points visited.

TABLE I

PERCENTAGE OF INPUT PML POINTS VISITED
(AVG. OF 30 INSTANCES).

| Budget (sec) | UAV only | UAV + UGV |
|---|---|---|
| 500 | 19 | 25 |
| 1000 | 36 | 49 |
| 1500 | 55 | 72 |

Figure 4C:
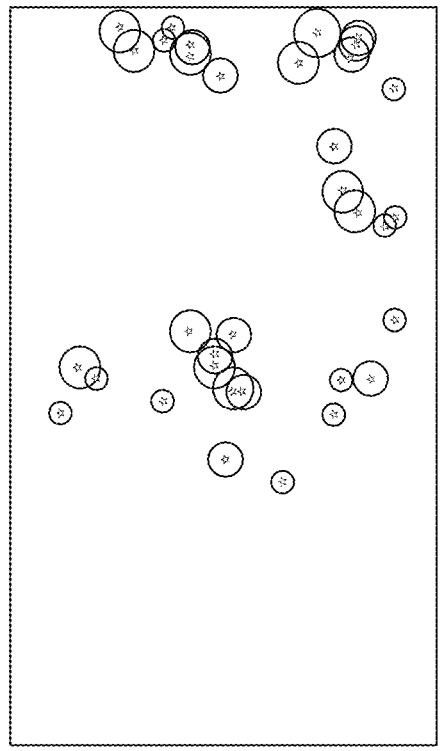
FIG. 4(c) shows a plan view of the geographic area of FIG. 4(a) showing the PML sampling areas that are not sampled using only an unmanned aerial vehicle.

The UAV+UGV system can cover points that are spread across the field. Intuitively, if the measurements are distributed across the field, it is expected that the resulting map (after incorporating the measurements) has fewer mislabeled points than if all measurements are nearby. After calculating the desired UAV/UGV tours, random measurements for the sensors were sampled directly from OM values given the dense (ground truth) GP. Noise was added to the measurements using estimated variances $\sigma_a=0.31$ and $\sigma_g=0.5$ as described above. These values were then used to update the prior GP, which was then used to find the posterior PML points. FIG. 4(c) shows the posterior PML points after the UAV-only sampling and FIG. 4(d) shown the posterior PML points after the combined UGV+UAV sampling.

Figure 6:
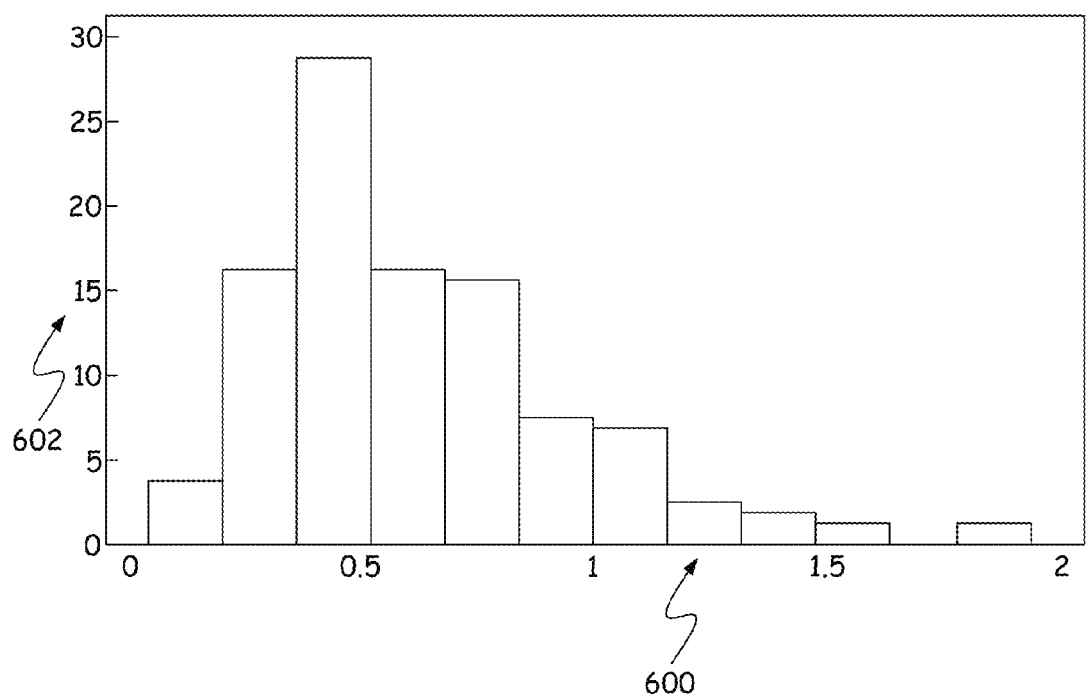
FIG. 6 provides a graph of the ratio of PML points left unvisited by an unmanned aerial vehicle and unmanned surface vehicle system over PML points left unvisited by an unmanned aerial vehicle alone.

FIG. 6 provides a histogram of the ratio of the number of PML points left in a field after the UAV+UGV system has sampled the field and the number of PML points left in the field after the UAV-system has sampled the field. In FIG. 6, the ratio value is shown along horizontal axis 600 and the number of fields is shown along vertical axis 602. Since the number of PML points depend on both the variance, and the estimated N(x) values, occasionally there are instances when the number of posterior PML points with the UAV-only system is less than that of UAV+UGV system. However, FIG. 6 shows that the UAV+UGV system often outperforms the UAV-only system in terms of number of posterior PML points.

This system obtains aerial images and soil samples with a UAV+UGV system to estimate a condition level in a plot. Effective treatment plans can be developed by better estimates of the current condition of various points of a field.

Since the battery life of a UAV is limited, the UAV and UGV can only sample a limited number of points. The embodiments described above maximize the number of points visited by the UAV and UGV. Unlike traditional approaches, the embodiments take into consideration the situation where the UAV can land on the UGV and thus be carried between points without expending energy.

In addition, the embodiments provide methods that identify a tour for UGV that will minimize the total cost of obtaining a sample for each disk around a PML point while ensuring that a sample is taken from each disk.

Figure 7:
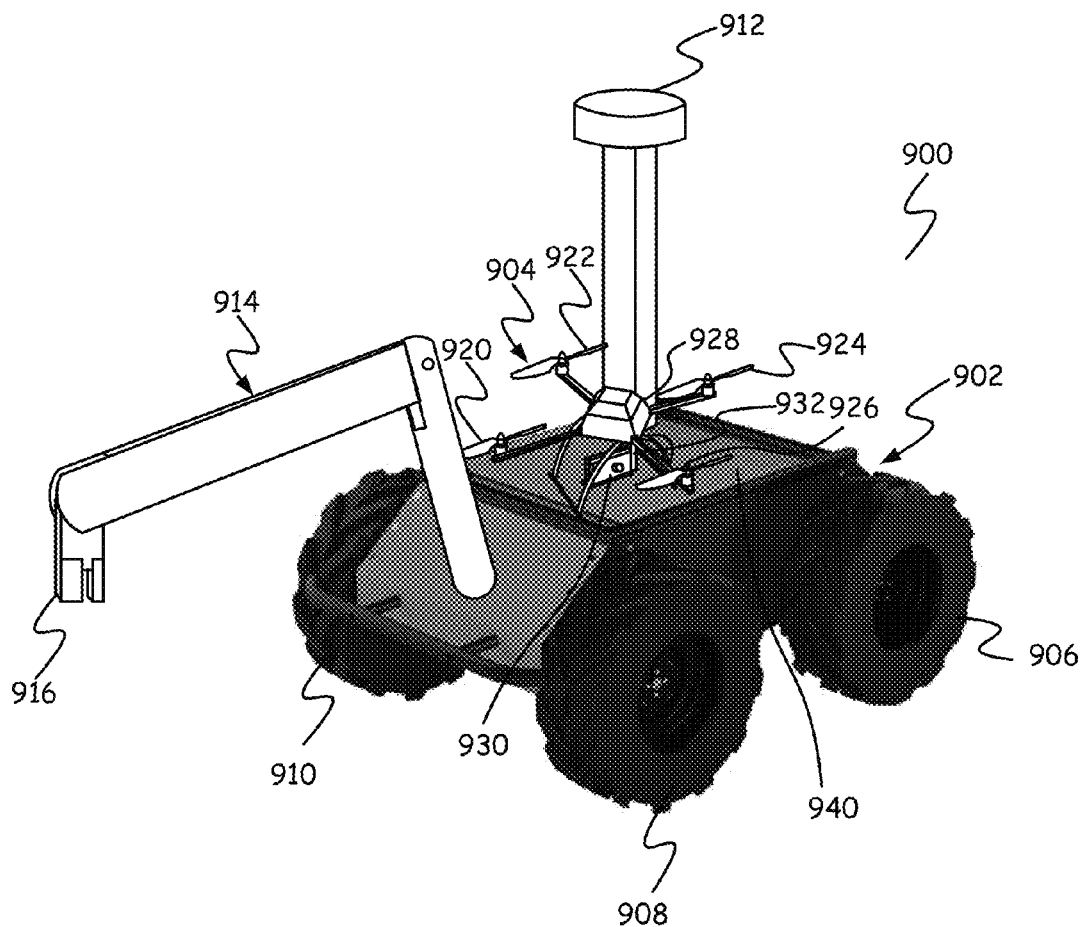
FIG. 7 provides a perspective view of an unmanned surface vehicle and unmanned aerial vehicle system in accordance with one embodiment.

FIG. 7 provides a perspective view of a measurement system 900 that includes an unmanned ground vehicle 902 and an unmanned aerial vehicle (aerial drone) 904. Unmanned ground vehicle 902 includes four rotatable wheels that include wheels 906, 908 and 910 and a fourth wheel that cannot be seen. Two or more of the wheels are rotated by internal motors under the control of a processor, described further below. Unmanned ground vehicle 902 also includes a GPS antenna assembly 912, which is used to receive a GPS signal from one or more satellites and can further include other antennas for wireless communication. Unmanned ground vehicle 902 includes other electronics that are not shown in FIG. 7 such as electronics used to control the operation of unmanned ground vehicle 902. Unmanned ground vehicle 902 also includes an articulated arm 914 that may be extended and rotated and that includes a sensor module 916 that includes one or more sensors such as a chlorophyll meter. Other sensors may be provided such as electric chemical sensors for detecting nitrogen ions in the soil, moisture content of soil and plant height.

Figure 9:
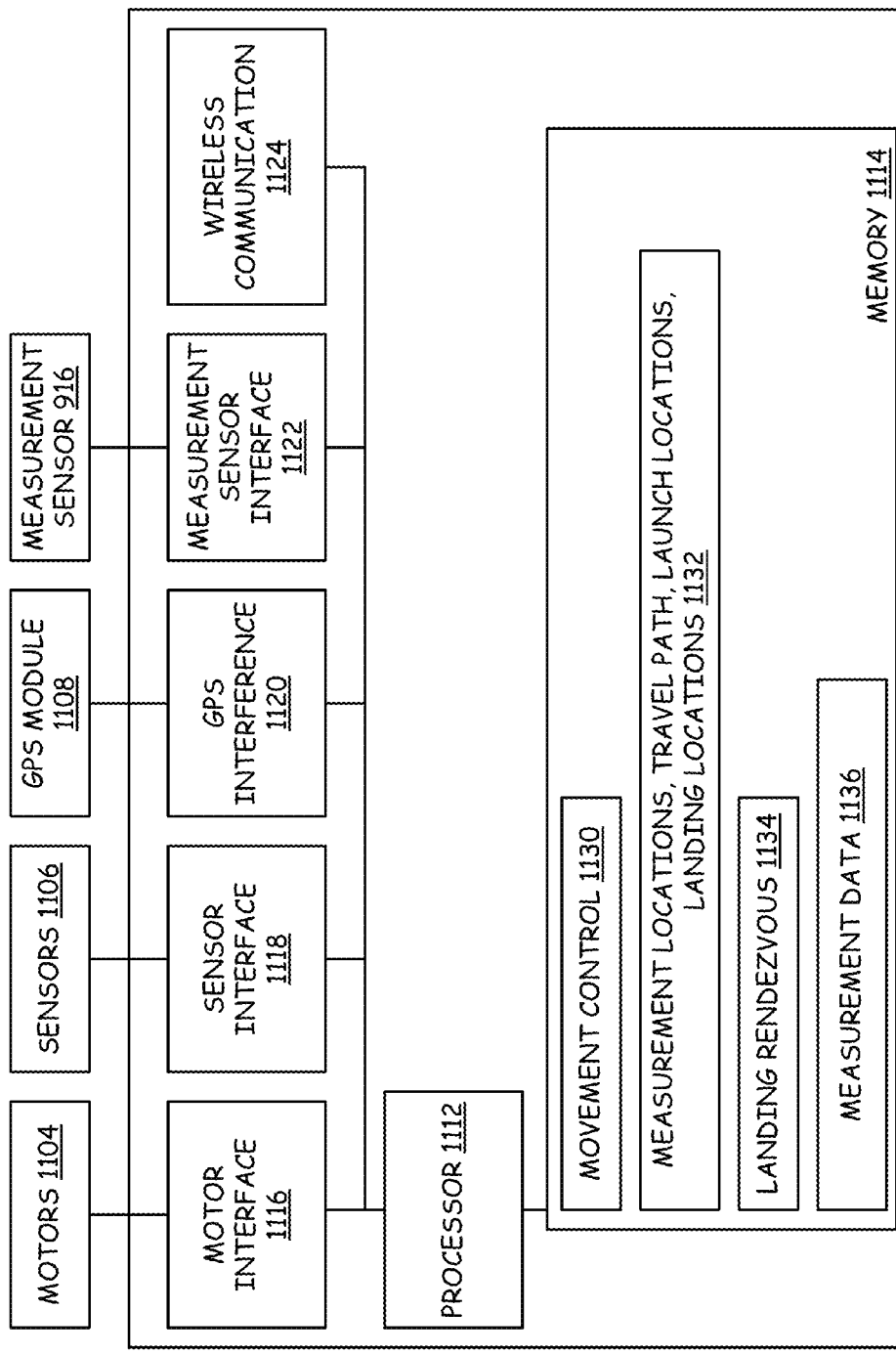
FIG. 9 provides a block diagram of elements found in an unmanned surface vehicle in accordance with one embodiment.

Unmanned aerial vehicle 904 includes four rotors 920, 922, 924 and 926 which are controlled by a printed circuit board in a central housing 928 and allow unmanned aerial vehicle 904 to launch from unmanned ground vehicle 902, to fly to preset locations and to rendezvous with unmanned ground vehicle 902 at a landing location where unmanned area vehicle 904 lands on landing deck 940 of unmanned ground vehicle 902. In FIG. 7, unmanned aerial vehicle 904 includes a camera 930 that can be rotated from a horizontal position as shown in FIG. 9 to a vertical position by control mechanisms 932 under housing 928. Thus, camera 930 can capture images with the lens of camera 930 pointing directly downward while unmanned aerial vehicle 904 is at an altitude above a field. Although a camera is shown, unmanned aerial vehicle 904 may include one or more additional measurement sensors in addition to or instead of camera 930.

In accordance with one embodiment, UGV 902 is a Husky A200 by Clearpath Robotics. The UGV has a typical battery life of two hours on a single charge. The operating lifetime can be extended to over six hours easily with additional batteries. The UGV will measure soil organic matter as a proxy for soil Nitrogen supply to the crop using a Minolta SPAD-502 Chlorophyll meter.

In accordance with one embodiment, UAV 904 is a Hexa XL by MikroKopter. This UAV can operate for 25 mins. Deploying the UAV to approximately 100 meters height gives the camera a 50 meter diameter coverage with a single image. The UAV takes about 2 minutes to ascend/descend this height. The images include multi-spectral information, such as near-infrared reflectance, which is used to estimate the crop N status.

Figure 8:
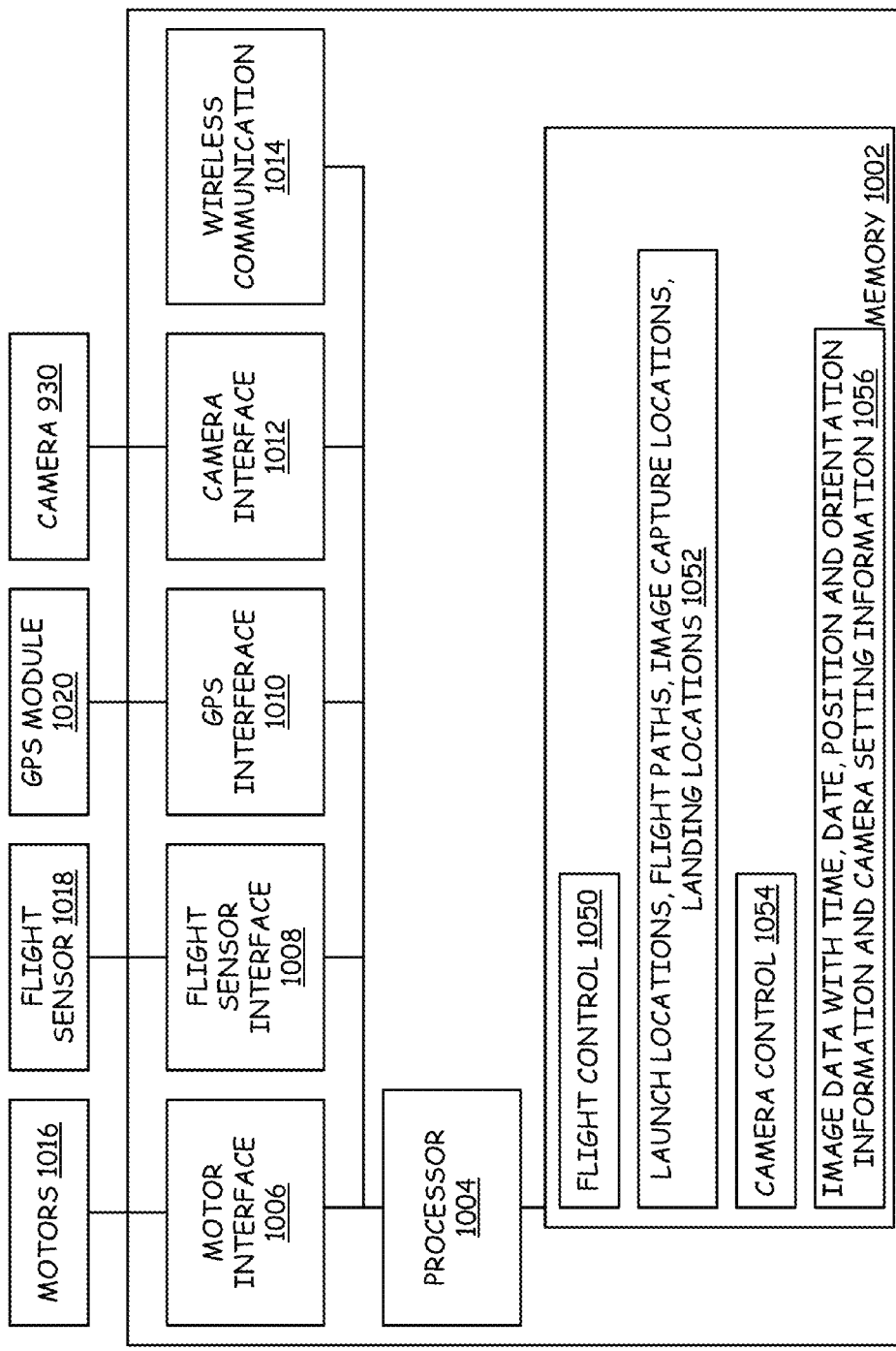
FIG. 8 provides a block diagram of elements found in an unmanned aerial vehicle in accordance with one embodiment.

FIG. 8 provides a block diagram of elements found in unmanned aerial vehicle 904 including a printed circuit board 1000, motors 1016, flight sensors 1018, and Global Positioning Satellite (GPS) module 1020. Although FIG. 8 shows a single printed circuit board 1000, the components on printed circuit board 1000 may be distributed across multiple printed circuit boards in unmanned aerial vehicle 904. Printed circuit board 1000 includes a memory 1002, a processor 1004, a motor interface 1006, a flight sensor interface 1008, GPS interface 1010, camera interface 1012 and a wireless communication module 1014. Motor interface 1006 acts as an interface between processor 1004 and one or more motors 1016 used to turn the rotors of unmanned aerial vehicle 904. Flight sensor interface 1008 provides an interface between processor 1004 and one or more flight sensors 1018 that are able to detect the orientation, velocity and acceleration of unmanned aerial vehicle 904 along three separate axes. Flight sensors 1018 can further determine pitch, roll and yaw of unmanned aerial vehicle 904. GPS interface 1010 provides an interface between GPS module 1020 and processor 1004. GPS module 1020 can detect signals from multiple satellites to determine a position of unmanned aerial vehicle 904. This position information can include a latitude and longitude of unmanned aerial vehicle 904 as well as the altitude of unmanned aerial vehicle 904. Camera interface 1012 provides an interface between processor 1004 and camera 930. Camera interface 1012 allows processor 1004 to set parameters for capturing images in camera 930 and to initiate the capturing of images. Camera interface 1012 also relays captured image data from camera 930 to processor 1004 for storage in memory 1002.

Wireless communication subsystem 1014 can include one or more communication modules for communicating with other devices using one or more communication protocols. For example, wireless communications 1014 can support wireless LAN, short-range radio communications, cellular data services and satellite communications. Wireless communication subsystem 1014 allows unmanned aerial vehicle 904 to communicate with unmanned ground vehicle 902 and/or a remote base station (not shown).

Memory 1002 includes data and computer-executable instructions to allow processor 1004 to launch unmanned aerial vehicle 904 from unmanned ground vehicle 902, to attain a desired altitude at a desired image capture location, to fly between image capture locations (also referred to as collection locations), and to rendezvous with unmanned ground vehicle 902 so as to land on unmanned ground vehicle 902. In particular, memory 1002 includes flight control instructions 1050 that are used by processor 1004 to control motors 1016 based on sensor data from flight sensors 1018 so that unmanned aerial vehicle 904 maintains stable flight and is able to launch, land and fly between way points along a path. Memory 1002 also includes launch locations, flight paths, image capture locations and landing locations 1052 which are used by processor 1004 to know where unmanned aerial vehicle 904 should be launched, where unmanned aerial vehicle 904 should fly to when it is launched, where camera 930 should be instructed to capture images along the flight path, and where unmanned aerial vehicle 904 should rendezvous with unmanned ground vehicle 902.

Memory 1002 also includes camera controls 1054 which are settings for camera 930 that are to be used when capturing images.

Image data captured by camera 930 is stored by processor 1004 along with time and date information, camera settings information and camera position and orientation information as image data 1056. Thus, for each image captured by camera 930, processor 1004 augments the image data with metadata that describes the time and date the image was captured, the position and orientation of camera 930 when the image was captured and the camera settings such as filters used by the camera when the image was captured.

FIG. 9 provides a block diagram of elements of unmanned ground vehicle 902 and includes a printed circuit board 1102, motors 1104, sensors 1106, GPS module 1108 and measurement sensors 1110. Although printed circuit board 1102 is shown as a single print circuit board, those skilled in the art will recognize that the components on printed circuit board 1102 can be distributed across multiple printed circuit boards.

Printed circuit board 1102 includes a processor 1112, a memory 1114, a motor interface 1116, a sensor interface 1118, a GPS interface 1120, a measurement sensor interface 1122 and a wireless communication module 1124.

Motor interface 1116 provides an interface between processor 1112 and motors 1104, which can include motors that turn the wheels of unmanned ground vehicle 902 and the motors that control articulated arm 914. Thus, through motor interface 1116, processor 1112 is able to move unmanned ground vehicle 902 and rotate, extend, and collapse articulated arm 914.

Sensor interface 1118 provides an interface between sensors 1106 and processor 1112. Sensors 1106 can include tilt sensors that sense the pitch or roll of unmanned ground vehicle 902, acceleration sensors that can sense the movement of unmanned ground vehicle 902 and touch sensors and image sensors that can detect the articulation and position of articulated arm 914 so as to provide the position of measurement sensors 916. GPS interface 1120 provides an interface between processor 1112 and a GPS module 1108. GPS module 1108 receives satellite signals and from those satellite signals determines a longitude and latitude of unmanned ground vehicle 902, which it provides to GPS interface 1120. GPS interface 1120 forwards this information to processor 1112, which then uses that information to position unmanned ground vehicle 902 at a desired position.

Measurement sensor interface 1122 provides an interface between processor 1112 and measurement sensors 1116. Through interface 1122, processor 1112 can instruct measurement sensor 916 to take a measurement at a current location and to provide the resulting measurement data. For example, processor 1112 can instruct measurement sensor 916 to measure the chlorophyll content in a plant leaf or to measure the amount of nitrogen in a soil sample.

Wireless communication system 1124 can include any form of desired wireless communication such as Wireless LAN, short-range radio communications and cellular data services. In particular, wireless communication module 1124 can communicate with wireless communication module 1014 of unmanned aerial vehicle 904 to allow unmanned ground vehicle 902 to coordinate with unmanned aerial vehicle 904 for the purposes of launching unmanned aerial vehicle 904 and recovering unmanned aerial vehicle 904. In further embodiments, wireless communication systems 1124 and 1014 can be used by unmanned aerial vehicle 904 and unmanned ground vehicle 902 to transmit images captured by unmanned aerial vehicle 904 to unmanned ground vehicle 902 so that the image data may be stored on unmanned ground vehicle 902 instead of on unmanned aerial vehicle 904 thereby reducing the power consumption of unmanned aerial vehicle 904. Wireless communication system 1124 can also be used to allow unmanned ground vehicle 902 to communicate with a remote base station (not shown).

Memory 1114 includes data and computer-executable instructions that allow unmanned ground vehicle 902 to travel between a set of stored locations, to obtain measurements at a set of measurement locations, to travel to one or more launch locations for launching unmanned aerial vehicle 904 and to rendezvous with unmanned aerial vehicle 904 to recover unmanned aerial vehicle 904. In particular, memory 1114 includes movement control instructions 1130 that are used by processor 1112 to control motors 1104 so that unmanned ground vehicle 902 moves along a desired path and does not pitch or roll excessively. Memory 1114 also includes travel data 1132 that includes measurement locations, travel paths, launch locations, and landing locations such that processor 1112 will use movement control instructions 1130 to move along the travel path, will instruct measurement sensor 916 to take measurements at each measurement location, will travel to launch locations along the travel path to allow unmanned aerial vehicle 904 to launch, and will travel to landing locations to recover unmanned aerial vehicle 904.

Memory 1114 also includes landing rendezvous instructions 1134 that allow unmanned ground vehicle 902 to determine whether to move to a next measurement location to take another measurement or to travel to a landing location to recover or rendezvous with unmanned aerial vehicle 904. The instructions associated with landing rendezvous 1134 are discussed in more detail in connection with FIG. 11.

Memory 1114 also includes measurement data 1136 provided by measurement sensor 916. Measurement data 1136 can include the measurements themselves as well as metadata provided by processor 1112 that indicates the location and time of day when the measurements were collected and the location where the measurements were taken.

Figure 10:
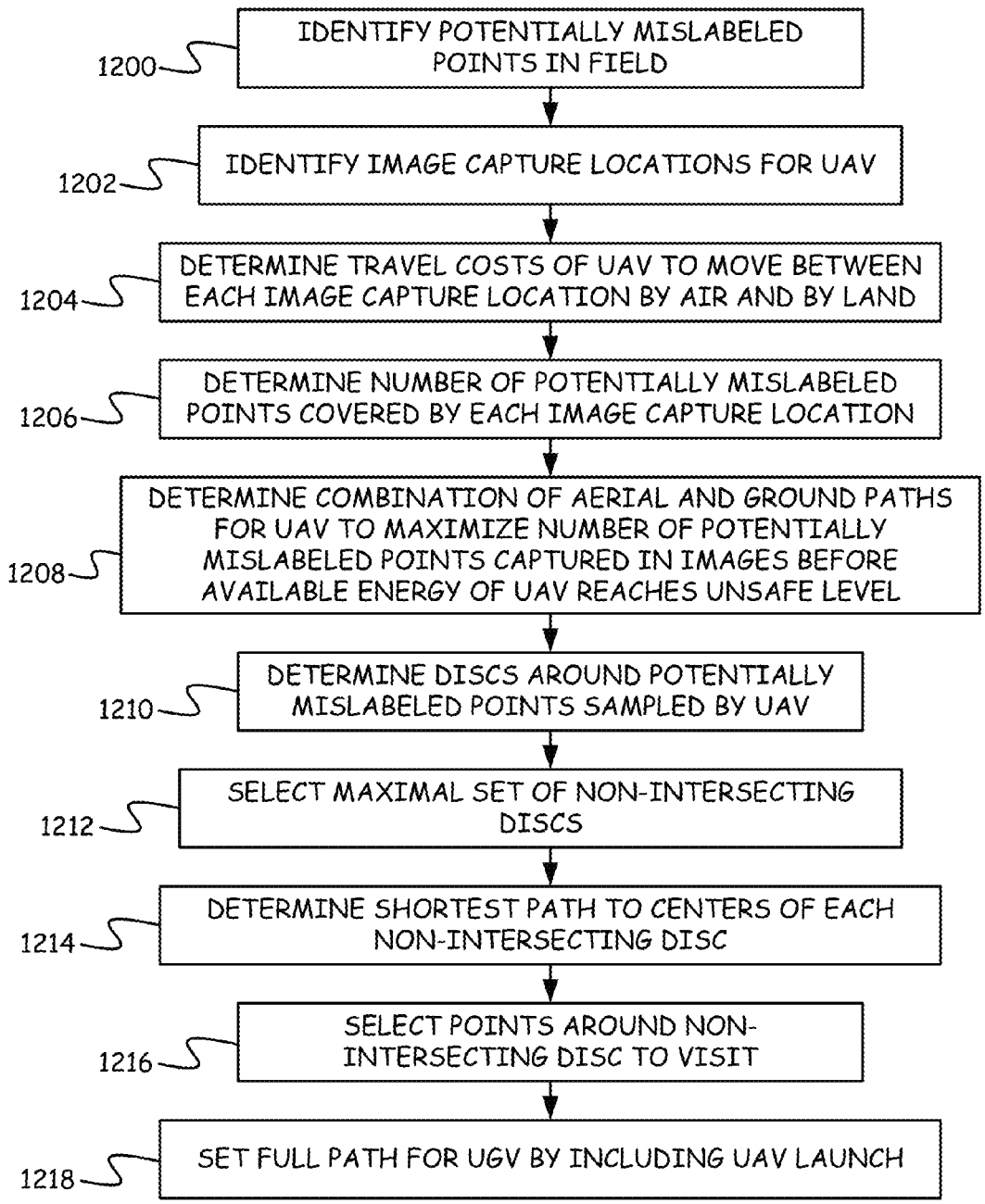
FIG. 10 provides a flow diagram for setting paths for a measurement system that includes both an unmanned aerial vehicle and unmanned surface vehicle where the unmanned surface vehicle carries the unmanned aerial vehicle along some paths.

FIG. 10 provides a flow diagram for setting paths for a measurement system that includes both an unmanned aerial vehicle and unmanned ground vehicle where the unmanned ground vehicle carries the unmanned aerial vehicle along some paths. At step 1200, potentially mislabeled points in a field are identified. In accordance with one embodiment, points in a field are potentially mislabeled if they are assigned to a class of condition levels (e.g., low nitrogen, medium nitrogen, and high nitrogen) and the most likely estimate of the condition at that location as well as the variance of the estimate provide a probability that the point is correctly labeled that is less than a threshold probability. Although nitrogen levels are specifically referenced, those skilled in the art will recognize that any desired measured parameter may be used such as moisture content or plant height. In such cases, the points are placed in different classes for the chosen parameter and a determination is made as to whether the probability of the point being in the right class is compared to the user-defined probability level.

At step 1202, image capture locations are identified for the unmanned aerial vehicle. In accordance with one embodiment, the image capture locations are identified by forming a grid of resolution $c/\sqrt{2}$ where c is the diameter of the area of the field captured by the camera in an image. The center point of each square grid that contains at least one of the mislabeled points from step 1200 is then identified as an image capture location.

At step 1204, travel costs for the unmanned aerial vehicle to move between each image capture location by air and by land are determined. In accordance with one embodiment, the energy cost for the unmanned aerial vehicle to move by air is the energy required to travel the Euclidean distance between the image capture locations. The energy cost for the unmanned aerial vehicle to move by land on top of the unmanned ground vehicle is set as the energy cost of landing the unmanned aerial vehicle and launching the unmanned aerial vehicle.

At step 1206, the number of potentially mislabeled points covered by each image capture location is determined. In other words, the number of potentially mislabeled points that appear in each of the grid squares is determined. Note that at least one of the grids will contain multiple potentially mislabeled points in most instances.

At step 1208, a combination of aerial and ground paths for the unmanned aerial vehicle is determined to maximize the number of potentially mislabeled points captured in images before an energy budget of the unmanned aerial vehicle is spent. To make this determination, the energy budget of the unmanned aerial vehicle is determined. In accordance with some embodiments, the unmanned aerial vehicle is said to have used all of its available energy or spent its energy budget when it has used enough of its available energy that the remaining energy reaches an unsafe level. Thus, there may be some energy still remaining in the energy source when the energy budget is spent to provide a margin of error for landing the unmanned aerial vehicle on its last flight. The margin of error should be adequate to account for high winds and unforeseen events.

The results of step 1208 are a set of launching locations, landing locations, and flying paths between the launching locations and the landing locations as well as a list of potentially mislabeled points that will be sampled by the UAV.

At step 1210, discs are constructed around the potentially mislabeled points that will be sampled by the UAV as found in step 1208. These discs represent an area within which a measurement must be taken in order for a label to be assigned to a potentially mislabeled point with a probability that exceeds the designated probability. As discussed above, the size of this disc is based on sensor noise and current uncertainty in the estimated parameter value and as such, each potentially mislabeled point can have a different disk size.

At step 1212, a maximal set of non-intersecting discs is selected. This maximal set includes the maximum number of non-intersecting discs that can be selected from the discs formed in step 1210. At step 1214, the shortest path to the centers of each non-intersecting disc is determined. At step 1216, points around the center of each non-intersecting disc are selected to be added to the path. As discussed above, this ensures that each of the discs identified in step 1210 will be visited by the unmanned ground vehicle. The points around the non-intersecting disc that do not lie within any of the discs of step 1210 may be removed from the path. At step 1218, the full path of the unmanned ground vehicle is determined by adding the unmanned aerial vehicle launch points to the paths. These launch points are be added so as to minimize the path length.

Figure 11:
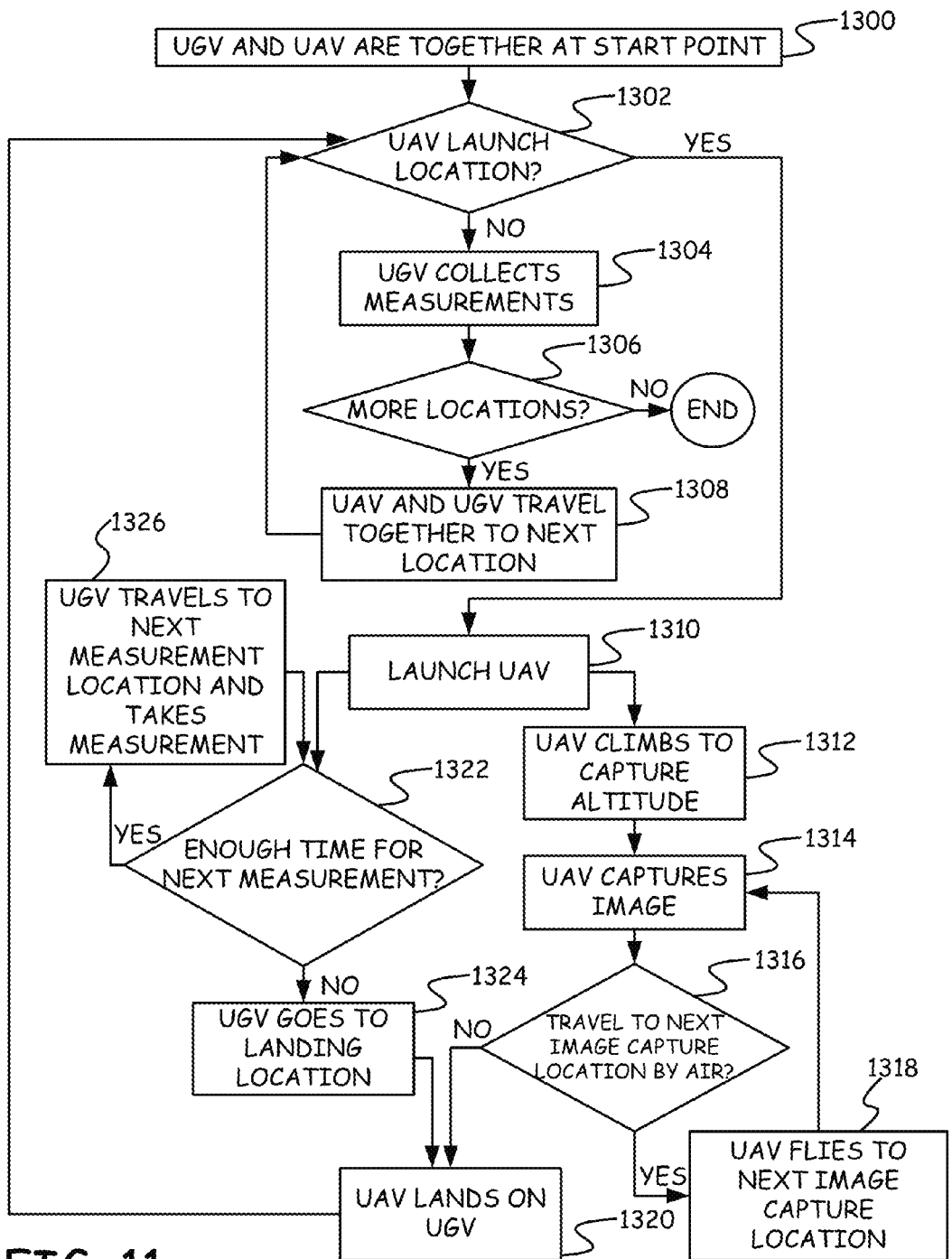
FIG. 11 provides a flow diagram of a measurement method using a system having an unmanned ground vehicle and an unmanned aerial vehicle.

FIG. 11 provides a flow diagram of a measurement method using a system having an unmanned ground vehicle and an unmanned aerial vehicle. At step 1300, the unmanned ground vehicle and unmanned aerial vehicle are placed together at a start point of the path determined at step 1218 of FIG. 10. At step 1302, the unmanned aerial vehicle and the unmanned ground vehicle both determine whether they are currently at an unmanned aerial vehicle launch location. If they are not an unmanned aerial vehicle launch location, they are at an unmanned ground vehicle measurement location. As such, at step 1304 the unmanned ground vehicle collects sensor measurements such as nitrogen levels or chlorophyll levels, for example. At step 1306, the unmanned ground vehicle determines if it is at the end of the path by determining if there are more locations within the path. If there are more locations, the unmanned aerial vehicle and the unmanned ground vehicle travel together to the next location at step 1308. Thus, the unmanned aerial vehicle is carried by the unmanned ground vehicle.

When the unmanned ground vehicle and unmanned aerial vehicle reach a launch location at step 1302, the unmanned aerial vehicle is launched at step 1310. At step 1312, the unmanned aerial vehicle climbs to a capture altitude to capture an image at step 1314. At step 1316, unmanned aerial vehicle 904 determines if it is to travel to the next image capture location by air. If it is to travel by air, the unmanned aerial vehicle flies to the next image capture location at step 1318 and captures a new image at step 1314. When the unmanned aerial vehicle is not to travel to the next image capture location by air but instead is to be carried by the unmanned ground vehicle to the next image capture location, the unmanned aerial vehicle lands on the unmanned ground vehicle at step 1320.

While unmanned aerial vehicle 904 is performing steps 1312, 1314, 1316 and 1318, unmanned ground vehicle 902 is executing landing rendezvous instructions 1134 to determine when to proceed to the unmanned aerial vehicle landing location. At step 1322 of the landing rendezvous instructions, unmanned ground vehicle 902 determines if there is enough time for a next ground measurement. To make this determination, processor 1112 of unmanned ground vehicle 902 determines the amount of time needed to travel to the next measurement location, the amount of time required to take a measurement at the measurement location, and the amount of time needed to travel from the next measurement location to the landing location. Those times are summed together and if the sum exceeds the time until an expected landing time, there is not enough time for a next measurement and the unmanned ground vehicle goes to the landing location at step 1324 so that the unmanned aerial vehicle can land on the unmanned ground vehicle at step 1320. The expected landing time can be set in the unmanned ground vehicle based on the time at which the unmanned aerial vehicle launched, an expected ascent time for the unmanned aerial vehicle to climb to the proper altitude for capturing images, expected travel times between image capture locations, expected time intervals for capturing images and an expected descent time needed for the unmanned aerial vehicle to descend and land on the unmanned ground vehicle.

If there is enough time for a next measurement at step 1322, the unmanned ground vehicle travels to the next measurement location and takes a measurement at step 1326. The rendezvous instructions continue at step 1322 by once again determining if there is time for another ground measurement. Steps 1322 and 1326 are repeated until the unmanned ground vehicle must go to the landing location to rendezvous with the unmanned aerial vehicle.

Although embodiments above have been discussed with reference to a field, the embodiments are not limited to taking samples in fields or to agricultural uses. In addition, although an unmanned ground vehicle has been discussed, in other embodiments an unmanned water vessel is used in place of the unmanned ground vehicle. Unmanned ground vehicles and unmanned water vessels are referred to generically as unmanned surface vehicles.

Although the present invention has been described with reference to preferred embodiments, workers skilled in the art will recognize that changes may be made in form and detail without departing from the spirit and scope of the invention.

What is claimed is:

1. A system comprising:
   an unmanned aerial vehicle having a memory storing a plurality of collection points and at least one sensor for collecting sensor data from each of the collection points;
   an unmanned surface vehicle capable of moving to a plurality of locations, the unmanned surface vehicle comprises a memory storing a plurality of soil measurement locations and a landing time and a landing location for the unmanned aerial vehicle and at least one soil sensor and wherein the unmanned surface vehicle collects at least one soil measurement using the at least one soil sensor at each of the soil measurement locations;
   wherein the unmanned aerial vehicle travels through the air between at least two collection points stored in the memory and wherein the unmanned aerial vehicle is carried between at least two collection points stored in the memory by the unmanned surface vehicle.

2. The system of claim 1 wherein the plurality of collection points comprise collection points selected from a larger set of possible collection points so as to maximize a number of measurement locations for which the unmanned aerial vehicle collects sensor data before an energy budget for the unmanned aerial vehicle is spent.

3. The system of claim 1 wherein the collection points are selected based on energy use by the unmanned aerial vehicle to travel between collection points and energy use by the unmanned aerial vehicle to launch and land.

4. The system of claim 3 wherein the unmanned aerial vehicle is carried on the unmanned surface vehicle between two collection points when the energy required for the unmanned aerial vehicle to fly between the two collection points exceeds the energy required for the unmanned aerial vehicle to land and launch from the unmanned surface vehicle.

5. The system of claim 1 wherein the unmanned surface vehicle travels to a next measurement location and collects at least one sensor signal at the next measurement location if a time needed to travel to the next measurement location, collect the at least one sensor signal and travel to the landing location is less than a time remaining until the landing time.

6. The system of claim 2 wherein the at least one sensor of the unmanned aerial vehicle comprises an image capture sensor and wherein the at least one sensor of the unmanned surface vehicle comprises a sensor for measuring Nitrogen levels.

7. The system of claim 6 wherein each measurement location comprises a location for which it is probable that an existing nitrogen classification of the location is incorrect.

8. A method comprising:
   storing measurement locations, launching locations, and landing locations in an unmanned surface vehicle's memory;
   storing image capture locations, launching locations and landing locations in an unmanned aerial vehicle's memory;
   initiating a data collection routine during which:
   the unmanned surface vehicle carries the unmanned aerial vehicle between multiple measurement locations and collects sensor data at the multiple measurement locations while the unmanned aerial vehicle is positioned on the unmanned surface vehicle;
   the unmanned surface vehicle carries the unmanned aerial vehicle to a launching location;
   the unmanned aerial vehicle launches from the launching location and flies to a plurality of image capture locations;
   the unmanned surface vehicle travels to a landing location; and
   the unmanned aerial vehicle lands on the unmanned surface vehicle at the landing location
   wherein the image capture locations, the launching locations and the landing locations are selected to maximize a number of measurement locations that are captured in images by the unmanned aerial vehicle before the unmanned aerial vehicle uses its budgeted energy.

9. The method of claim 8 wherein after the unmanned aerial vehicle is launched and before the unmanned aerial vehicle lands, the unmanned surface vehicle travels to a measurement location from the launching location and collects sensor data at the measurement location.

10. The method of claim 8 wherein each measurement location comprises a location in a farm field that is suspected of having an incorrect nitrogen classification.

11. The method of claim 8 wherein the unmanned aerial vehicle comprises a camera with a field of view at a selected altitude such that at each image capture location the field of view of the camera at the selected altitude includes a view of at least one measurement location.

12. The method of claim 11 wherein the field of view of the camera at the selected altitude for at least one image capture location includes a view of multiple measurement locations.

13. A method comprising:
    identifying a collection of areas in which measurements should be taken;
    finding a maximal set of non-intersecting areas among the collection of areas;
    setting an initial tour to a point in each area in the maximal set of non-intersecting areas;
    finding a minimum number of sampling locations around each area in the maximal set of non-intersecting areas in order to ensure that there is at least one sampling location in each area of the collection of areas;
    adjusting the initial tour to add each sampling location to form an adjusted tour; and
    instructing an unmanned vehicle to travel along the adjusted tour and to collect measurements at the point in each area in the maximal set of non-intersecting disks and each sampling location.

14. The method of claim 13 wherein the unmanned vehicle comprises an unmanned surface vehicle.

15. The method of claim 14 further comprising:
    determining launching and landing locations for an unmanned aerial vehicle carried by the unmanned surface vehicle;
    determining a tour for the unmanned aerial vehicle between each launching and landing location; and
    instructing the unmanned aerial vehicle to fly along the tour and collect images of areas in the collection of areas positioned along the tour.

16. The method of claim 15 wherein the unmanned surface vehicle carries the unmanned aerial vehicle between one landing location and one launch location.

17. The method of claim 13 wherein at least one sampling location is in more than one of the areas in the collection of areas.

* * * * *

UNITED STATES PATENT AND TRADEMARK OFFICE
CERTIFICATE OF CORRECTION

| | |
|---|---|
| PATENT NO. | : 9,464,902 B2 |
| APPLICATION NO. | : 14/498369 |
| DATED | : October 11, 2016 |
| INVENTOR(S) | : Volkan Isler et al. |

It is certified that error appears in the above-identified patent and that said Letters Patent is hereby corrected as shown below:

In the Specification

Please replace Equation (2) in Column 5 with the following:

$$N(x_i) = \mu_p + K_\theta(x_i, X_p) K_\theta(X_p, X_p)^{-1}(N(X_p) - \mu_p)$$

$$\sigma(x_i)^2 = \sigma_p^2 - K_\theta(x_i, X_p) K_\theta(X_p, X_p)^{-1} K_\theta(x_i, X_p)^T$$

(2)

Please replace Equation (4) in Column 5 with the following:

$$l_j^*(x_i) = \min\left(|N(x_i) - l_j^-|, |N(x_i) - l_j^+|\right)$$

(4)

Signed and Sealed this
Fourteenth Day of February, 2017

Michelle K. Lee
*Director of the United States Patent and Trademark Office*